(12) United States Patent
Vedrine et al.

(10) Patent No.: US 10,335,556 B2
(45) Date of Patent: Jul. 2, 2019

(54) APPARATUS AND METHODS FOR LOW-VOLUME MEDICAMENT DELIVERY

(71) Applicant: Genentech, Inc., South San Francisco, CA (US)

(72) Inventors: Lionel Vedrine, Palo Alto, CA (US); Ariel Waitz, San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 476 days.

(21) Appl. No.: 14/560,163

(22) Filed: Dec. 4, 2014

(65) Prior Publication Data
US 2015/0157810 A1 Jun. 11, 2015

Related U.S. Application Data

(60) Provisional application No. 61/912,628, filed on Dec. 6, 2013.

(51) Int. Cl.
*A61M 5/34* (2006.01)
*A61M 5/315* (2006.01)
(Continued)

(52) U.S. Cl.
CPC .......... *A61M 5/345* (2013.01); *A61M 5/3134* (2013.01); *A61M 5/31531* (2013.01);
(Continued)

(58) Field of Classification Search
CPC . A61M 5/345; A61M 5/3134; A61M 5/31531
See application file for complete search history.

(56) References Cited

U.S. PATENT DOCUMENTS

| 2,656,836 A | 10/1953 | Hickey |
| 2,811,155 A * | 10/1957 | Dunnican ............... A61M 5/34 604/242 |

(Continued)

FOREIGN PATENT DOCUMENTS

| CN | 2472735 | 1/2002 |
| CN | 2671595 | 1/2005 |

(Continued)

OTHER PUBLICATIONS

Cambridge university, Materials Data Book, 2003 pp. 1-39.*

(Continued)

*Primary Examiner* — Edelmira Bosques
(74) *Attorney, Agent, or Firm* — Weiss & Arons LLP

(57) ABSTRACT

Apparatus and methods for delivering medicament. The apparatus may include a fitting for a fluid dispenser. The fitting may include a detent that is configured to limit insertion of the dispenser into the fitting by contacting a terminal surface of the dispenser; and a seal for sealing against the surface. The apparatus may include an insert for the fitting. The insert may include a gasket to seal against the terminal surface of the dispenser; a proximal rim to engage a lateral wall of the dispenser; and a connector fixed to the gasket and the rim. The apparatus may include a coupler to engage a pre-filled dispenser; and a body defining a passageway that is configured to be placed in fluid communication with the dispenser. The apparatus may include a dispenser that includes a detent and a seal. The detent may limit insertion of the dispenser into a fitting.

33 Claims, 15 Drawing Sheets

(51) Int. Cl.
*A61M 5/31* (2006.01)
*A61M 5/32* (2006.01)
*B65D 83/28* (2006.01)

(52) U.S. Cl.
CPC ............ *A61M 5/3293* (2013.01); *B65D 83/28* (2013.01); *A61M 5/347* (2013.01); *A61M 2005/3103* (2013.01)

(56) References Cited

U.S. PATENT DOCUMENTS

| | | | |
|---|---|---|---|
| 3,498,135 A * | 3/1970 | Seitz et al. | B01L 3/0217 422/564 |
| 4,938,745 A * | 7/1990 | Sagstetter | A61M 5/002 128/917 |
| 5,112,327 A | 5/1992 | Iinuma et al. | |
| 5,320,603 A | 6/1994 | Vetter et al. | |
| 5,330,443 A | 7/1994 | Powles et al. | |
| 5,374,250 A | 12/1994 | Dixon | |
| 5,513,630 A | 5/1996 | Century | |
| 5,584,817 A | 12/1996 | van den Haak | |
| 5,591,137 A * | 1/1997 | Stevens | A61M 39/0613 604/167.04 |
| 5,685,866 A | 11/1997 | Lopez | |
| 5,902,271 A | 5/1999 | Jentzen | |
| 5,964,737 A | 10/1999 | Caizza | |
| 6,210,375 B1 | 4/2001 | Moulton et al. | |
| 6,217,556 B1 | 4/2001 | Ellingson et al. | |
| 6,245,044 B1 | 6/2001 | Daw et al. | |
| 6,344,034 B1 | 2/2002 | Sudo et al. | |
| 6,423,033 B1 | 7/2002 | Tsai | |
| 6,454,745 B1 | 9/2002 | Donnan et al. | |
| 6,626,869 B1 | 9/2003 | Bint | |
| 6,648,849 B2 | 11/2003 | Tenhuisen et al. | |
| 6,699,221 B2 | 3/2004 | Vaillancourt | |
| 6,726,649 B2 | 4/2004 | Swenson et al. | |
| 6,761,706 B2 | 7/2004 | Vaillancourt | |
| 6,800,067 B2 | 10/2004 | Lee | |
| 6,902,543 B1 | 6/2005 | Cherif-Cheikh et al. | |
| 6,913,595 B2 | 7/2005 | Mastorakis | |
| 6,942,643 B2 | 9/2005 | Eakins et al. | |
| 6,960,195 B2 | 11/2005 | Heinz et al. | |
| 7,090,657 B2 | 8/2006 | Tang | |
| 7,252,653 B2 | 8/2007 | Ueda et al. | |
| 7,527,607 B2 | 5/2009 | Botich et al. | |
| 7,544,182 B2 | 6/2009 | Kiehne | |
| 7,670,318 B2 | 3/2010 | Alesi et al. | |
| 7,776,018 B2 | 8/2010 | Bush, Jr. et al. | |
| 7,837,659 B2 | 11/2010 | Bush, Jr. et al. | |
| 7,918,821 B2 | 4/2011 | Mahurkar | |
| 7,998,120 B2 | 8/2011 | Sano et al. | |
| 8,092,445 B2 | 1/2012 | Reymond et al. | |
| 8,197,451 B2 | 6/2012 | Zihlmann et al. | |
| RE43,597 E | 8/2012 | Johnson et al. | |
| 8,287,484 B2 | 10/2012 | Rockley | |
| 8,414,560 B2 | 4/2013 | Bush, Jr. et al. | |
| 8,419,688 B2 | 4/2013 | Woehr et al. | |
| 8,454,564 B2 | 6/2013 | Deppisch et al. | |
| 8,460,247 B2 | 6/2013 | Woehr et al. | |
| 8,491,533 B2 | 7/2013 | Parihar et al. | |
| 8,512,299 B2 | 8/2013 | Shams | |
| 8,529,525 B2 | 9/2013 | Gerber et al. | |
| 8,551,047 B2 | 10/2013 | Burns et al. | |
| 8,551,074 B2 | 10/2013 | Hoffman et al. | |
| 8,568,367 B2 | 10/2013 | Griffiths et al. | |
| 8,940,251 B2 | 1/2015 | Watanabe | |
| 2001/0018575 A1 | 8/2001 | Lyza, Jr. | |
| 2003/0040720 A1 | 2/2003 | Steube | |
| 2004/0186427 A1 | 9/2004 | Pok | |
| 2004/0210196 A1 | 10/2004 | Bush, Jr. et al. | |
| 2008/0033347 A1 | 2/2008 | D'Arrigo et al. | |
| 2008/0039800 A1 | 2/2008 | Bush, Jr. et al. | |
| 2008/0269697 A1 | 10/2008 | Bush et al. | |
| 2009/0143746 A1 | 6/2009 | Mudd et al. | |
| 2010/0049143 A1 | 2/2010 | D'Arrigo et al. | |
| 2010/0137813 A1 | 6/2010 | Mudd et al. | |
| 2010/0160870 A1 | 6/2010 | Clements et al. | |
| 2011/0015572 A1 | 1/2011 | Thorley et al. | |
| 2011/0028909 A1 | 2/2011 | Lum et al. | |
| 2011/0034882 A1 | 2/2011 | Quinn et al. | |
| 2011/0077602 A1 | 3/2011 | Yokota et al. | |
| 2011/0092784 A1 | 4/2011 | Butler et al. | |
| 2011/0202035 A1 | 8/2011 | Voellmicke et al. | |
| 2011/0282298 A1 | 11/2011 | Agian et al. | |
| 2011/0313317 A1 | 12/2011 | Callicoat et al. | |
| 2012/0037266 A1 | 2/2012 | Bochenko | |
| 2012/0083749 A1 | 4/2012 | Kawamoto et al. | |
| 2012/0095409 A1 | 4/2012 | Lanin et al. | |
| 2012/0197210 A1 | 8/2012 | Kuhn et al. | |
| 2012/0259313 A1 | 10/2012 | Krumme et al. | |
| 2013/0165860 A1 | 6/2013 | Doud et al. | |
| 2013/0172818 A1 | 7/2013 | Schraga | |
| 2013/0184654 A1 | 7/2013 | Drake et al. | |
| 2013/0197485 A1 | 8/2013 | Gardner et al. | |
| 2013/0204206 A1 | 8/2013 | Morgan et al. | |
| 2013/0211376 A1 | 8/2013 | McCulloch et al. | |
| 2013/0218120 A1 | 8/2013 | Rosenquist et al. | |
| 2013/0218121 A1 | 8/2013 | Waller et al. | |
| 2013/0289517 A1 | 10/2013 | Williams et al. | |
| 2013/0331801 A1 | 12/2013 | Hoffman et al. | |
| 2014/0039404 A1 | 2/2014 | Young et al. | |
| 2014/0114284 A1 | 4/2014 | Rowe et al. | |

FOREIGN PATENT DOCUMENTS

| | | |
|---|---|---|
| CN | 102470215 | 5/2012 |
| EP | 2311512 | 4/2011 |
| RU | 2009/135627 | 4/2011 |
| WO | WO95/13839 | 5/1995 |
| WO | WO1995013839 | 5/1995 |
| WO | WO2006/088858 | 8/2006 |
| WO | WO2006088858 | 8/2006 |
| WO | WO2008/016710 | 2/2008 |
| WO | WO2008016710 | 2/2008 |
| WO | WO2008/114223 | 9/2008 |
| WO | WO2011112916 | 9/2011 |

OTHER PUBLICATIONS

International Search Report for International Application No. PCT/US2014/068516, dated Mar. 16, 2015.
Intellectual Property Office of Singapore Written Opinion in application No. 11201604189Q, dated Jun. 27, 2017.
(EPO) Communication Pursuant to Article 94(3) EPC in application No. 14828593.5, dated Dec. 4, 2017.
Office Action in Russian Application No. 2016126413, dated Jun. 7, 2018.
Search Report in Russian Application No. 2016126413, dated Jun. 7, 2018.
Australian Patent Office Examination Report in Application No. 2014360486, dated Oct. 24, 2018.
Federal Institute of Industrial Property in Russia, Office Action in Application No. 2016126413, dated Oct. 25, 2018.
State Intellectual Property Office of China Official Action in Chinese Application No. 2014800659553, dated Nov. 28, 2018.
English translation of State Intellectual Property Office of China Official Action in Chinese Application No. 2014800659553, dated Nov. 28, 2018.

* cited by examiner

APPARATUS AND METHODS FOR LOW-VOLUME MEDICAMENT DELIVERY

CROSS-REFERENCE TO RELATED APPLICATIONS

This application claims the benefit of U.S. Provisional Application No. 61/912,628, filed on Dec. 6, 2013, which is hereby incorporated by reference herein in its entirety.

BACKGROUND OF THE INVENTION

A medicament in liquid form is commonly delivered into a patient through a needle. A dispenser such as a syringe may be used to deliver the medicament through the needle. The syringe is often connected to the needle by a connector. The syringe, connector and needle form a pathway for delivery of the medicament. Some of the medicament may leave the pathway and enter into void space in the connector and thus not be delivered to the patient. Often, the void space is small relative to the volume of medicament that is to be delivered. In such cases, the therapeutic and economic consequences of losing medicament from the pathway may be acceptable. Sometimes, however, the loss is not acceptable. For example, the void space may be large relative to the volume of medicament that is to be delivered, the medicament may be expensive, the loss may make dosing unpredictable because the loss may vary in volume from one connector to another, among other reasons.

It would be desirable, therefore, to provide apparatus and methods for reducing the loss of medicament from the delivery pathway.

Dispensers such as syringes are often prefilled with a desired medicament volume. A practitioner then fully depresses a plunger in the syringe to deliver the medicament into the patient. Prefilling the syringe reduces the likelihood of overfilling or underfilling by a practitioner. Fully depressing the plunger of the syringe reduces the likelihood of underdosing the patient, assuming that the prefilled volume is correct.

Volumetric precision of prefilling a large volume may be greater than the volumetric precision of prefilling a small volume. When it is desirable to prefill the dispenser for the delivery of a small volume, the lack of volumetric precision may be unacceptable. It would be desirable, therefore, to provide apparatus and methods for using a dispenser to deliver a small volume of the medicament to the patient.

DETAILED DESCRIPTION OF THE DISCLOSURE

Figures 1, 2:
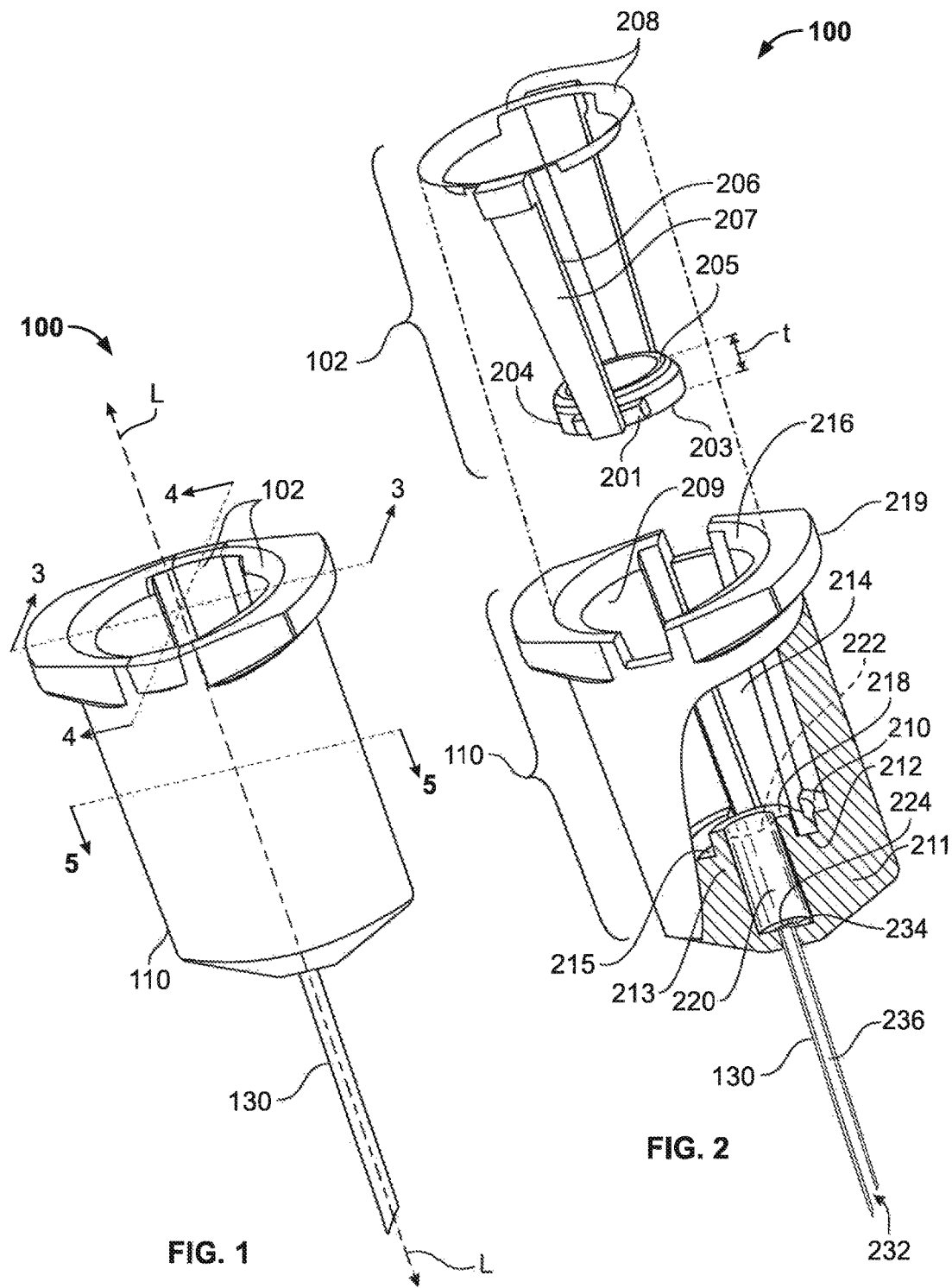
FIG. 1 is a perspective view of apparatus in accordance with the principles of the invention.
FIG. 2 is an exploded perspective view of the apparatus shown in FIG. 1, including a partial cross-sectional view of internal features of the apparatus.

Apparatus and methods for using a dispenser to deliver a small volume of a medicament to a patient are provided. The apparatus may be used to perform one or more steps of the methods.

The dispenser may be a pre-filled syringe. The apparatus may include a fitting to provide fluid communication along a fluid pathway between the medicament dispenser and a needle. The apparatus may include a seal to reduce loss of fluid from the fluid pathway. The seal may be part of the fitting. The seal may be part of the dispenser. The seal may be part of an insert for the fitting. The apparatus may include a reservoir along the fluid pathway. The reservoir may be part of the fitting. The reservoir may be part of the dispenser. The reservoir may retain fluid to accommodate use of the dispenser when the dispenser has excess medicament.

The medicament may include a formulation of one or more compounds. The compounds may include naturally occurring substances. The compounds may include substances derived from naturally occurring substances. The compounds may include synthetically produced substances. The compounds may include chimeric substances. The compounds may include engineered substances. The compounds may include humanized substances. The compounds may include substances produced by recombinant techniques. The compounds may include substances modified by recombinant techniques.

The compounds may include a drug accepted for therapeutic treatment of a patient. The compounds may include a substance used in a therapeutic protocol. The compounds may include a substance used in a diagnostic protocol. The compounds may include a substance used in an experimental protocol. The compounds may include a substance compatible for use with apparatus and methods of the invention.

Illustrative medicaments that may be used with the apparatus may include any of those listed herein, either alone or in combination with each other or with other, non-listed, medicaments. The medicaments may include anti-glaucoma medications, other ocular agents, neuroprotective agents, antimicrobial agents, anti-inflammatory agents (including steroids and non-steroidal compounds), and biological agents including hormones, enzymes or enzyme-related components, antibodies or antibody-related components, oligonucleotides (including DNA, RNA, short-interfering RNA, and other suitable oligonucleotides, such as antisense oligonucleotides), DNA/RNA vectors, viruses or viral vectors, peptides, and proteins. The medicaments may include anti-angiogenesis agents, including angiostatin, anecortave acetate, thrombospondin, vascular endothelial growth factor (VEGF) receptor tyrosine kinase inhibitors, and anti-VEGF drugs, such as ranibizumab (LUCENTIS®), bevacizumab (AVASTIN®), pegaptanib (MACUGEN®), sunitinib, and sorafenib, and any of a variety of known small-molecule and transcription inhibitors having an anti-angiogenesis effect; ophthalmic drugs, including glaucoma agents, such as adrenergic antagonists, including beta-blocker agents such as atenolol, propranolol, metipranolol, betaxolol, carteolol, levobetaxolol, levobunolol and timolol. The medicaments may include anti-inflammatory agents including glucocorticoids and corticosteroids, such as betamethasone, cortisone, dexamethasone, dexamethasone 21-phosphate, methylprednisolone, prednisolone 21-phosphate, prednisolone acetate, prednisolone, loteprednol, medrysone, fluocinolone acetonide, triamcinolone acetonide, triamcinolone, beclomethasone, budesonide, flunisolide, fluorometholone, fluticasone, hydrocortisone, hydrocortisone acetate and rimexolone; and non-steroidal anti-inflammatory agents including diclofenac, flurbiprofen, ibuprofen, bromfenac, nepafenac, ketorolac, salicylate, indomethacin, naxopren, naproxen, piroxicam and nabumetone. The medicaments may include anti-complement agents, including those targeting complement factor D (such as an anti-complement factor D antibody or an antigen-binding fragment thereof) and those targeting complement factor H (such as an anti-complement factor H antibody or an antigen-binding fragment thereof).

In descriptions herein of apparatus and methods of the invention, the term "seal" and the term "gasket" may be used interchangeably. In descriptions herein of apparatus and methods of the invention, functions of the reservoir may be performed by a void or passageway in fluid communication with the fitting.

Fitting

The fitting may receive the end of the dispenser to place the dispenser in fluid communication with the needle. The fitting may have a longitudinal axis. The fitting may include a detent. The detent may be configured to limit longitudinal insertion of the dispenser into the fitting. The limitation may be effected by application, by the detent, of a longitudinal contact force against a terminal surface of the dispenser.

Prior to the fitting receiving the end of the dispenser, the seal may be in a relaxed state. The seal may be configured to be deformed by the inserted terminal surface of the dispenser. The seal may be configured to be deformed into sealing contact against the terminal surface. The seal may be deformed into sealing contact against the terminal surface when the terminal surface abuts, or lodges against, the detent. Were application of the longitudinal contact force to cease, the seal may be configured to return substantially to its relaxed state.

The seal may include a first seal material. The first seal material may include rubber. The first seal material may include silicone. The first seal material may include a thermoplastic elastomer (TPE). The first seal material may include a polymeric substance. The first seal material may include a material with a hardness less than about 200 Shore A durometer (ASTM D2240 type A hardness scale).

The seal may include a second seal material. The second seal material may include polytetrafluoroethylene (PTFE). The second seal material may include ethylene tetrafluoroethylene (ELTFE). The second seal material may coat the first seal material. The second seal material may include a material selected to reduce interaction of the seal with a medicament.

The seal may be configured such that the seal would not return substantially to its relaxed state upon cessation of application of the longitudinal contact force. The seal may be configured to remain substantially deformed. The seal may be configured for one-time use.

The seal may be configured to be crushed to provide sealing contact between the fitting and the dispenser. The seal may be configured as a crushable bib between the fitting and the dispenser. Prior to the fitting receiving the end of the dispenser, the crushable bib may be associated with the dispenser. Prior to the fitting receiving the end of the dispenser, the crushable bib may be associated with the fitting.

The fitting may include a body. The body may be configured to receive the terminal surface of the dispenser. The body may be configured to support the detent. The detent may lie within a plane disposed on a portion of the body. The detent may overlie a portion of the body. The detent may be a portion of the body. The detent may be within the body.

The body may include a body material. The body material may include polypropylene (hereinafter, "PP"). The body material may include polyethylene (hereinafter, "PE"). The body material may include polycarbonate (hereinafter, "PC"). The body material may include a rigid material. The body material may include a semi-rigid material. The body material may include a transparent material. The body material may include a translucent material. The body material may include an opaque material. The body material may include a material that is chemically inert. The body material may include a material that is chemically stable. The body material may include a material selected for having minimum interaction with a medicament.

The body may be configured to support the seal. The seal may be a portion of the body. The seal may be installed in the body. The seal may be within the body.

The seal may circumscribe the detent. The detent may circumscribe the seal.

The fitting may define an opening. The opening may be configured to be placed in fluid communication with the dispenser. The opening may be transverse to the longitudinal axis. The longitudinal axis may run through the opening. The longitudinal axis may run through the center of the opening. The detent may define the opening. The seal may define the opening.

The fitting may include an interior wall. The interior wall may be an interior circumferential wall of the body. The interior circumferential wall may have a cylindrical axis. When the dispenser is coupled to the fitting, the cylindrical axis may be collinear with the longitudinal axis of the fitting.

The dispenser may include a lateral wall. The lateral wall may be an exterior circumferential wall of the dispenser. When the dispenser is a syringe, the lateral wall may be an exterior circumferential wall of a syringe barrel. A portion of the wall of the barrel may be complementary to the interior circumferential wall of the body. The portion may be received within the interior circumferential wall of the body. The portion may be received within the interior circumferential wall of the body through longitudinal insertion of the dispenser into the fitting.

The dispenser may have a distal end. The distal end may have a distal tip. The lateral wall may be an exterior circumferential wall of the distal tip. A portion of the exterior circumferential wall of the distal tip may be complementary to the interior circumferential wall of the body. A portion of the exterior circumferential wall of the distal tip may be received within the interior circumferential wall of the body. The portion of the exterior circumferential wall of the distal tip may be received within the interior circumferential wall of the body through longitudinal insertion of the dispenser into the fitting.

The distal end of the dispenser may have a distal-most face. The terminal surface of the dispenser may coincide with the distal-most face of the dispenser.

The dispenser may include a dispenser material. The dispenser material may include glass. The dispenser material may include a polymeric substance. The dispenser material may include a crystalline polymer. The dispenser material may include an amorphous polymer. The dispenser material may include a cyclic olefin polymer (COP). The dispenser material may include a cyclic olefin copolymer (COC). The dispenser material may include PP. The dispenser material may include PE. The dispenser material may include PC. The dispenser material may include a transparent material. The dispenser material may include a translucent material. The dispenser material may include an opaque material. The dispenser material may include a material that is chemically inert. The dispenser material may include a material that is chemically stable. The dispenser material may include a material selected for having minimum interaction with a medicament.

The distal-most face of the dispenser may define an aperture in fluid communication with an interior volume of the dispenser. The aperture may be in fluid communication with a bore of the syringe. The distal end of the dispenser may be received by the fitting through longitudinal insertion, distal-end first, of the dispenser into the fitting. Insertion of the distal end of the dispenser into the fitting may be limited by the distal-most face coming into contact with the detent supported by the body. The dispenser may be selected, or may be modified, so that the distal-most face of its distal end may come into contact with the detent upon longitudinal insertion into the fitting.

When the terminal surface of the dispenser is in sealing contact against the seal, a volumetric region may be defined by the interior wall of the fitting, the lateral wall of the dispenser and the seal. When the terminal surface of the dispenser abuts the detent, the interior wall, the lateral wall and the seal may define the region. When the terminal surface of the dispenser is in sealing contact against the seal and abuts the detent, the interior wall, the lateral wall and the seal may define the region.

The region may be isolated from fluid communication with the dispenser. The sealing contact may be sufficient to prevent leakage of fluid from the dispenser to the region when the dispenser is actuated to dispense the fluid. The region may be isolated from fluid communication with the opening. The sealing contact may be sufficient to prevent leakage of fluid from the opening to the region when the dispenser is actuated to dispense the fluid.

The region may be a first dead space. The first dead space may have a first volume.

When the detent is in contact with the terminal surface of the dispenser, the detent may define a second dead space. The second dead space may include one or more volumes in a region that is transversely coextensive with contact of the detent and the surface and that longitudinally extends between the detent and the surface. The second dead space may be bordered by an inner annular boundary of the seal.

The second dead space may have a second volume. The second volume may be no more than 1% the first volume. The second volume may be no more than 0.1% the first volume.

The body of the fitting may define a void. The void may be a reservoir. The void may be a passageway. The void may be in fluid communication with the opening. The void may have a void volume.

The dispenser may be pre-filled with an initial volume of the fluid. The void volume may be not less than 10% the initial volume of fluid in the dispenser. The void volume may be not less than 25% the initial volume. The void volume may be not less than 50% the initial volume. The void volume may be not less than 75% the initial volume. The void volume may be not less than 90% the initial volume.

The fitting may support the needle. The needle may be in fluid communication with the void. Fluid may be dispensed through an orifice of the needle. The orifice may be a delivery orifice of the needle. A volume of fluid dispensed through the orifice may be the initial volume reduced by an amount. The amount may be not less than the void volume. The amount may include a volume remaining in the dispenser after the fluid is dispensed. The amount may include a volume of a bore of the needle.

The seal may be annular. The seal may be rectilinear. The seal may be any shape that provides effective sealing.

The seal may include a proximal face. The seal may include a distal face. The distal face may be spaced apart from the proximal face. The proximal face and the distal face may be substantially parallel.

The seal may include an outer surface. The outer surface may extend in the longitudinal direction. The seal may include an inner surface. The inner surface may extend in the longitudinal direction.

The distal face and the inner surface may intersect at an angle of about 90°. The distal face and the inner surface may intersect at an angle that may range from about 80° to about 89°. The distal face and the inner surface may intersect at an angle that may range from about 70° to about 79°. The distal face and the inner surface may intersect at an angle that may range from about 60° to about 69°. The distal face and the inner surface may intersect at an angle that may range from about 50° to about 59°. The distal face and the inner surface may intersect at an angle that may range from about 40° to about 49°. The distal face and the inner surface may intersect at an angle that may range from about 91° to about 100°. The distal face and the inner surface may intersect at an angle that may range from about 101° to about 110°. The distal face and the inner surface may intersect at an angle that may range from about 111° to about 120°. The distal face and the inner surface may intersect at an angle that may range from about 121° to about 130°. The distal face and the inner surface may intersect at an angle that may range from about 131° to about 140°.

The distal face and the inner surface may be configured such that they do not intersect. One or more other seal surfaces may lie between the distal face and the inner surface. The other seal surfaces may connect the distal face and the inner surface. The other seal surfaces may form one or more corners between the distal face and the inner surface.

The distal face and the outer surface may intersect at an angle of about 90°. The distal face and the outer surface may intersect at an angle that may range from about 80° to about 89°. The distal face and the outer surface may intersect at an angle that may range from about 70° to about 79°. The distal face and the outer surface may intersect at an angle that may range from about 60° to about 69°. The distal face and the outer surface may intersect at an angle that may range from about 50° to about 59°. The distal face and the outer surface may intersect at an angle that may range from about 40° to about 49°. The distal face and the outer surface may intersect at an angle that may range from about 91° to about 100°. The distal face and the outer surface may intersect at an angle that may range from about 101° to about 110°. The distal face and the outer surface may intersect at an angle that may range from about 111° to about 120°. The distal face and the outer surface may intersect at an angle that may range from about 121° to about 130°. The distal face and the outer surface may intersect at an angle that may range from about 131° to about 140°.

The distal face and the outer surface may be configured such that they do not intersect. One or more other seal surfaces may lie between the distal face and the outer surface. The other seal surfaces may connect the distal face and the outer surface. The other seal surfaces may form one or more corners between the distal face and the outer surface.

The proximal face and the inner surface may intersect at an angle of about 90°. The proximal face and the inner surface may intersect at an angle that may range from about 80° to about 89°. The proximal face and the inner surface may intersect at an angle that may range from about 70° to about 79°. The proximal face and the inner surface may intersect at an angle that may range from about 60° to about 69°. The proximal face and the inner surface may intersect at an angle that may range from about 50° to about 59°. The proximal face and the inner surface may intersect at an angle that may range from about 40° to about 49°. The proximal face and the inner surface may intersect at an angle that may range from about 91° to about 100°. The proximal face and the inner surface may intersect at an angle that may range from about 101° to about 110°. The proximal face and the inner surface may intersect at an angle that may range from about 111° to about 120°. The proximal face and the inner surface may intersect at an angle that may range from about 121° to about 130°. The proximal face and the inner surface may intersect at an angle that may range from about 131° to about 140°.

The proximal face and the inner surface may be configured such that they do not intersect. One or more other seal surfaces may lie between the proximal face and the inner surface. The other seal surfaces may connect the proximal face and the inner surface. The other seal surfaces may form one or more corners between the proximal face and the inner surface.

The proximal face and the outer surface may intersect at an angle of about 90°. The proximal face and the outer surface may intersect at an angle that may range from about 80° to about 89°. The proximal face and the outer surface may intersect at an angle that may range from about 70° to about 79°. The proximal face and the outer surface may intersect at an angle that may range from about 60° to about 69°. The proximal face and the outer surface may intersect at an angle that may range from about 50° to about 59°. The proximal face and the outer surface may intersect at an angle that may range from about 40° to about 49°. The proximal face and the outer surface may intersect at an angle that may range from about 91° to about 100°. The proximal face and the outer surface may intersect at an angle that may range from about 101° to about 110°. The proximal face and the outer surface may intersect at an angle that may range from about 111° to about 120°. The proximal face and the outer surface may intersect at an angle that may range from about 121° to about 130°. The proximal face and the outer surface may intersect at an angle that may range from about 131° to about 140°.

The proximal face and the outer surface may be configured such that they do not intersect. One or more other seal surfaces may lie between the proximal face and the outer surface. The other seal surfaces may connect the proximal face and the outer surface. The other seal surfaces may form one or more corners between the proximal face and the outer surface.

The seal may have a cross-section. The cross-section may include a substantially square profile. The cross-section may include a substantially rectangular profile. The cross-section may have substantially perpendicular corners. The cross-section may be substantially trapezoidal. The cross-section may have substantially rounded corners. The cross-section may be substantially circular. The cross-section may be substantially ovoid. The cross-section may be substantially ellipsoid. The cross-section may include any combination of straight lines and/or curves that provides effective sealing.

The fitting may include a base portion. The detent and the seal may extend longitudinally from the base portion in a proximal direction. The detent may include a top. The seal, in a relaxed state, may extend proximally beyond the top. The seal may not extend transversely over the top.

The base portion may define a recess. The recess may be configured to receive the seal. The recess may have a cross-section that is complementary to a portion of the cross-section of the seal. The recess may be configured to secure the seal. The seal may be secured such that a proximal end of the seal does not relax over the top.

When the terminal surface of the dispenser abuts the detent, the terminal surface may be perpendicular to the longitudinal axis of the fitting. When the terminal surface of the dispenser abuts the detent, the terminal surface may be at an orientation other than perpendicular to the longitudinal axis of the fitting.

When the terminal surface of the dispenser abuts the detent, the terminal surface may be oriented to the longitudinal axis at an angle that may range from about 80° to about 89°. When the terminal surface of the dispenser abuts the detent, the terminal surface may be oriented to the longitudinal axis at an angle that may range from about 70° to about 79°. When the terminal surface of the dispenser abuts the detent, the terminal surface may be oriented to the longitudinal axis at an angle that may range from about 60° to about 69°. When the terminal surface of the dispenser abuts the detent, the terminal surface may be oriented to the longitudinal axis at an angle that may range from about 50° to about 59°. When the terminal surface of the dispenser abuts the detent, the terminal surface may be oriented to the longitudinal axis at an angle that may range from about 40° to about 49°. When the terminal surface of the dispenser abuts the detent, the terminal surface may be oriented to the longitudinal axis at an angle that may range from about 91° to about 100°. When the terminal surface of the dispenser abuts the detent, the terminal surface may be oriented to the longitudinal axis at an angle that may range from about 101° to about 110°. When the terminal surface of the dispenser abuts the detent, the terminal surface may be oriented to the longitudinal axis at an angle that may range from about 111° to about 120°. When the terminal surface of the dispenser abuts the detent, the terminal surface may be oriented to the longitudinal axis at an angle that may range from about 121° to about 130°. When the terminal surface of the dispenser abuts the detent, the terminal surface may be oriented to the longitudinal axis at an angle that may range from about 131° to about 140°.

When the terminal surface of the dispenser abuts the detent, the terminal surface may be at an orientation to the longitudinal axis of the fitting at any angle that lodges the terminal surface of the dispenser against the detent. When the terminal surface of the dispenser abuts the detent, the terminal surface may be at an orientation to the longitudinal axis of the fitting at any angle that provides effective sealing of the seal against the terminal surface.

The detent may have a first contour. The terminal surface of the dispenser may have a second contour. The first contour and the second contour may be complementary. The seal may have a third contour. The second contour and the third contour may be complementary.

The seal may include a first substance. The first substance may include the first seal material. The first substance may include the second seal material. The first substance may have a first elastic modulus. The detent may include a second substance. The second substance may include the body material. The second substance may have a second elastic modulus. The second elastic modulus may be greater than the first elastic modulus.

The terminal surface of the dispenser may be disposed on a portion of the dispenser that includes a third substance. The third substance may include the dispenser material. The third substance may have a third elastic modulus. The third elastic modulus may be about the same as the second elastic modulus.

The fitting may include an engagement member. The engagement member may be configured to maintain the sealing contact. The engagement member may maintain the sealing contact by engaging the dispenser. The dispenser may have a complementary engagement surface that the engagement member may engage. The engagement member may be a Luer-style surface in the fitting. The dispenser may have a complementary engagement surface that may engage the Luer-style surface of the fitting. The Luer-style surface of the fitting and the complementary surface of the dispenser may be of a Luer lock variety. The Luer-style surface of the fitting and the complementary surface of the dispenser may be of a Luer slip variety.

The fitting may include one or more bosses. The one or more bosses may be associated with the interior wall of the fitting. Each of the one or more bosses may be configured to extend radially inward relative to the cylindrical axis from the interior circumferential wall of the fitting. The one or more bosses may be configured to engage the dispenser. The one or more bosses may be configured to engage the lateral wall of the dispenser.

The fitting may be configured to engage a needle guard. The guard may cover the needle prior to dispensing the fluid. The guard may be configured to be disassociated from the fitting prior to dispensing the fluid.

The fitting may be packaged for use by a practitioner with the needle guard engaged with the fitting. The dispenser may be packaged for use by the practitioner pre-filled with the initial volume of the fluid. The fitting may be packaged for use together with the pre-filled dispenser. Packaging may maintain sterility of the packaged items.

The pre-filled dispenser may be capped by a cap. The cap may be removed from the dispenser prior to the fitting being engaged with the dispenser. The needle guard may be removed from the fitting subsequent to the fitting being engaged with the dispenser.

The seal and the fitting may be a unitary piece. The unitary piece may include a fourth substance. The unitary piece may be semi-rigid. The seal may be integral to the fitting. The fourth substance may have an elastic modulus less than the second elastic modulus and greater than the first elastic modulus.

Insert

The insert may engage the terminal surface of the dispenser. The insert may engage the lateral wall of the dispenser when the fitting receives the dispenser. The insert may be seated in the fitting.

The insert may include a first material. The first material of the insert may include the first seal material. The first material of the insert may include the second seal material. The fitting may include a second material. The second material of the fitting may include the body material. The first material of the insert may be more compliant than the second material of the fitting. The insert may include a distal gasket. The gasket may be configured to seal against a terminal surface of a dispenser. The gasket may have one or more features in common with the seal.

The insert may include a proximal rim. The proximal rim may be configured to engage a lateral wall of the dispenser. The proximal rim engaging the lateral wall of the dispenser may supplement other engagement of the lateral wall. Other engagement of the lateral wall may be achieved through urging the gasket against the terminal surface. The proximal rim urging the gasket against the terminal surface may supplement any urging of the gasket against the terminal surface that may be achieved through engagement of the fitting with the dispenser The insert may include one or more connectors. Each of the one or more connectors may be distally fixed to the gasket. Each of the one or more connectors may be proximally fixed to the rim. The gasket and the rim may be substantially parallel. The gasket and the rim may be mutually oriented in a non-parallel orientation. The gasket and the rim may be spaced apart, at least in part, by the one or more connectors. Each of the one or more connectors may have at least one substantially longitudinal member. The at least one longitudinal member may be fixed to the rim. Each of the one or more connectors may have at least one substantially transverse member. The at least one transverse member may be fixed to the gasket.

The gasket may be configured to be seated in a recess in the fitting. Each of the one or more connectors may be configured to be seated in a recess in the fitting.

The rim may be configured to conform to a flange of the fitting. The rim may be configured to conform to the engagement member. The flange of the fitting may be associated with a proximal edge of a circumferential wall of the fitting. The engagement member may be associated with a proximal end of the fitting. The proximal edge may be associated with the proximal end.

The one or more connectors may be configured to transmit force between the gasket and the rim. The force may urge the gasket against the terminal surface of the dispenser. The connector may urge the gasket against the terminal surface by transmitting the force between the gasket and the rim. The force may urge the rim against the lateral surface of the dispenser. The connector may urge the rim against the lateral surface by transmitting the force between the gasket and the rim.

The insert may be molded onto the fitting. The molding may be accomplished through an overmolding process. The molding may be accomplished through a coinjection process. The recesses into which the connectors may be seated may expedite molding of the insert. The recesses may provide channels for a seal material of the insert, injectable during a molding process, to flow between the proximal end of the fitting and the recess into which the gasket may be seated. The injectable seal material may form the gasket. The injectable material may form the rim. The rim may be a remnant of the molding process of the gasket. The injectable material may form the one or more connectors. The one or more connectors may be remnants of the molding process of the gasket. The one or more connectors may be configured to not transmit the force between the gasket and the rim.

Reservoir

The reservoir may retain a volume of fluid when the dispenser is actuated to dispense fluid. The reservoir may include a coupler. The coupler may have one or more features in common with the fitting. The coupler may have one or more features in common with the seal. The coupler may sealingly engage a dispenser. The dispenser may be pre-filled with an initial volume of fluid. The reservoir may be included in the fitting. The reservoir may be included in the dispenser. When the reservoir is included in the dispenser, the fitting may be configured such that it does not include a reservoir.

The reservoir may include the passageway. The passageway may be configured to be placed in fluid communication with the dispenser. The passageway may lead to a hypodermic needle. The needle may be in fluid communication with the passageway.

The passageway may have a volume. The volume of the passageway may be not less than 10% of the initial volume of fluid in the dispenser. The volume of the passageway may be not less than 25% of the initial volume. The volume of the passageway may be not less than 50% of the initial volume. The volume of the passageway may be not less than 75% of the initial volume. The volume of the passageway may be not less than 90% of the initial volume.

Fluid may be dispensed through a delivery orifice of the hypodermic needle. The volume of fluid dispensed through the delivery orifice may be the initial volume reduced by an amount. The amount may be not less than the volume of the passageway.

The methods for low volume medicament delivery may involve dispensing a dose volume of substance from the dispenser. The dispenser may be pre-filled with an initial volume of the substance. The substance may include the medicament.

The methods may include a multi-stage discharging of liquid from the dispenser. A first stage may include discharging a priming volume from the dispenser. The priming volume may be discharged by depressing a plunger of the dispenser to a first mechanically indexed position within the bore of the dispenser. The first position may be indexed by a collar on a proximal end of a shaft of the plunger. The collar may be configured to allow the plunger to be advanced distally within the bore sufficiently, and no more than is required, to drive the priming volume out of the bore. The collar may be removed from the shaft after the priming volume is discharged from the bore. At least part of the priming volume may be driven into the reservoir. At least part of the priming volume may be driven into the needle.

A second stage may include depressing the plunger to a second mechanically indexed position within the bore. The second position may be indexed by the proximal end of the shaft contacting a proximal end of the dispenser. The second position may be indexed by the proximal end of the shaft contacting a proximal end of the bore. The second position may be indexed by the proximal end of the shaft contacting stop surface external to the bore. The second position may be indexed by a distal end of the shaft contacting a stop shoulder internal to the bore. The distal end of the shaft may include a plunger plug. The second position may accommodate a maximum stroke of the plunger within the bore.

The volume of fluid discharged from the dispenser in the second stage may be the dose volume. The dose volume may correspond to the initial prefilled volume minus the priming volume.

The method may include retaining a reservoir volume in the reservoir. The reservoir volume may be part of the priming volume. The reservoir volume may be not less than 10% of the initial volume of substance with which the dispenser may be pre-filled. The reservoir volume may be not less than 25% of the initial volume. The reservoir volume may be not less than 50% of the initial volume. The reservoir volume may be not less than 75% of the initial volume. The reservoir volume may be not less than 90% of the initial volume.

The reservoir may be in fluid communication with the dispenser. The reservoir may be in fluid communication with a needle. The needle may include a delivery orifice.

The method may include dispensing the dose volume through the delivery orifice of the needle. The dose volume may be the initial volume reduced by an amount. The amount may be not less than the reservoir volume.

Dispenser

A fluid dispenser may be configured to include a seal for sealingly engaging a fitting. The fluid dispenser may include the dispenser material. The fitting may include the body material. The seal may include the first seal material. The seal may include the second seal material. The fluid dispenser may have a distal end that includes the seal. When the distal end includes the seal, the fitting may be configured such that it does not include a seal.

The distal end may include a detent. The detent may be transverse to the longitudinal axis of the dispenser. The detent may be configured to limit longitudinal insertion of the dispenser into a fitting. Longitudinal insertion of the dispenser into the fitting may be limited by the detent applying a longitudinal contact force against a proximal surface of the fitting.

The seal may be configured to be deformed by the proximal surface of the fitting. The seal may be configured to be deformed into sealing contact against the surface. The seal may be deformed into sealing contact against the surface when the detent lodges against the surface.

The distal end may include a terminal portion. The terminal portion may be configured to be received by the fitting. The terminal portion may be configured to support the detent. The terminal portion may be configured to support the seal. The seal may circumscribe the detent. The detent may circumscribe the seal.

The distal end detent may define an aperture. The detent may define an aperture. The aperture may be in fluid communication with a bore of the dispenser. The fitting may define a passageway configured to be placed in fluid communication with the aperture.

The terminal portion may include an exterior lateral wall. The fitting may include an interior wall. When the seal may be in sealing contact against the proximal surface of the fitting and the detent may abut the surface, the exterior wall, the interior wall and the seal may define a region.

The sealing contact may be sufficient to prevent leakage of fluid from the dispenser to the region when the dispenser may be actuated to dispense the fluid. The region may be isolated from fluid communication with the dispenser.

The region may be a first dead space. The first dead space may have a first volume.

When the detent is in contact with the proximal surface of the fitting, the detent may define a second dead space. The second dead space may include one or more volumes in a region that may be transversely coextensive with contact between the detent and the surface and may be longitudinally extensive between the detent and the surface. The second dead space may be within the seal.

The second dead space may have a second volume. The second volume may be no more than 1% the first volume. The second volume may be no more than 0.1% the first volume.

The detent and the seal may extend longitudinally from a section of the terminal portion in a distal direction. The detent may include a bottom. The seal, in a relaxed state, may extend distally beyond the bottom. The seal may not extend transversely under the bottom.

The terminal portion section may define a recess. The recess may be configured to secure the seal. The recess may be annular. The seal may be annular. The seal may be configured to engage the recess. The seal may circumferentially engage the recess. The seal may adhere to a surface of the recess. The seal may be secured such that a distal end of the seal may not be drawn laterally under the bottom.

When the detent lodges against the proximal surface of the fitting, the surface may be perpendicular to the longitudinal axis of the dispenser.

The detent may have a first contour. The proximal surface of the fitting may have a second contour. The first contour and the second contour may be complementary. The seal may have a third contour. The second contour and the third contour may be complementary.

The proximal surface of the fitting may be disposed on a portion of the fitting having a third elastic modulus. The third elastic modulus may be about the same as the second elastic modulus.

The dispenser may include an engagement member. The engagement member may be configured to maintain the sealing contact. The engagement member may maintain the sealing contact by engaging the fitting.

The dispenser may include a glass syringe.

The bore of the dispenser may have a bore diameter. The dispenser may include a plunger. The plunger may have a plunger plug. The plunger plug may have a diameter about the same as the bore diameter. The plunger plug may be slideably disposed within the bore. The plunger plug may be moved within the bore longitudinally distally toward the aperture from a proximal position. Longitudinal movement of the plunger plug toward the aperture may drive fluid in the bore toward the aperture.

The bore may include a shoulder jutting radially into the bore. The shoulder may be annular. The shoulder may have an inner annular diameter smaller than the bore diameter. The shoulder may be located between the plunger plug and the aperture. Movement of the plunger plug within the bore to the aperture may be stopped by the shoulder.

A volume of the bore between the shoulder and the aperture may serve a purpose similar to that of the reservoir, void or passageway described above.

The fitting may include a detent, a seal and a reservoir (or void). Alternatively, the dispenser may include the detent, the seal and the reservoir (or void). In other embodiments, only one of the detent, the seal and the reservoir may be in the fitting, with the others being in the dispenser. In yet other embodiments, two of the detent, the seal and the reservoir may be in the fitting, with the other being in the dispenser.

Apparatus and methods in accordance with the invention will now be described in connection with the FIGS. The FIGS. show illustrative features of apparatus and methods in accordance with the principles of the invention. The features are illustrated in the context of selected embodiments. It will be understood that features shown in connection with one of the embodiments may be practiced in accordance with the principles of the invention along with features shown in connection with another of the embodiments.

Apparatus and methods described herein are illustrative. Apparatus and methods of the invention may involve some or all of the features of the illustrative apparatus and/or some or all of the steps of the illustrative methods. The steps of the methods may be performed in an order other than the order shown and described herein. Some embodiments may omit steps shown and described in connection with the illustrative methods. Some embodiments may include steps that are not shown and described in connection with the illustrative methods.

Illustrative embodiments will now be described with reference to the accompanying drawings, which form a part hereof.

The apparatus and methods of the invention will be described in connection with embodiments and features of illustrative devices. The devices will be described now with reference to the FIGS. It is to be understood that other embodiments may be utilized and structural, functional and procedural modifications may be made without departing from the scope and spirit of the present invention.

FIG. 1 shows illustrative device 100. Device 100 may define longitudinal axis L.

Device 100 may include fitting 110. Device 100 may include insert 102. FIG. 1 shows that insert 102 may be seated in fitting 110.

Device 100 may include needle 130. Needle 130 may be supported by fitting 110. Needle 130 may be in fluid communication with fitting 110. Needle 130 may be a hypodermic needle. Needle 130 may be parallel to axis L.

FIG. 2 shows that insert 102 may include distal gasket 204. Gasket 204 may be annular.

Gasket 204 may include proximal face 205. Gasket 204 may include distal face 203. Face 203 and face 205 may be substantially parallel to each other. Face 203 and face 205 may be spaced apart by thickness t.

Insert 102 may include proximal rim 208. Rim 208 and gasket 204 may be substantially parallel to each other.

Insert 102 may include one or more connectors between rim 208 and gasket 204. For example, insert 102 may include connector 206. Rim 208 and gasket 204 may be spaced apart by connector 206. Connector 206 may be connected proximally to rim 208. Connector 206 may be connected distally to gasket 204.

Connector 206 may include transverse member 201. Connector 206 may include longitudinal member 207. Member 201 may be connected to member 207. Member 201 and member 207 may be components of a unitary body. Member 201 may be connected to gasket 204. Member 207 may be connected to rim 208. Rim 208, gasket 204 and connector 206 may be components of the unitary body. The unitary body may include insert 102.

Insert 102 may be seated in fitting 110 (as shown in FIG. 1). Rim 208 may be separately seated in fitting 110 (not shown). Gasket 204 may be separately seated in fitting 110 (not shown).

Fitting 110 may include body 211. Body 211 may include flange 216. Rim 208 may engage flange 216. Body 211 may include engagement member 219. Rim 208 may engage engagement member 219.

Body 211 may include interior wall 209. Interior wall 209 may include longitudinal recess 214. Connector 206 may be seated in recess 214. Member 207 may be seated in recess 214.

Body 211 may include recess 212. Recess 212 may be complementary to a distal portion of gasket 204. Recess 212 may be annular. Gasket 204 may be seated in recess 212. When gasket 204 is seated in recess 212, face 203 may contact distal bottom 215 of recess 212.

Body 211 may include facet 210. Body 211 may include base portion 213. Base portion 213 may include recess 212. When gasket 204 is seated in recess 212, base portion 213 may support gasket 204.

Base portion 213 may support detent 218. Detent 218 may define opening 222. Detent 218 may circumscribe opening 222.

Body 211 may include void 220. Opening 222 may be a proximal end of void 220. Opening 222 may be in fluid communication with void 220.

Body 211 may include floor 224. Floor 224 may be a distal boundary of void 220. Floor 224 may include needle inlet 234. Needle inlet 234 may be connected with needle 130.

Needle 130 may include needle bore 236. Bore 236 may be in fluid communication with inlet 234. Needle 130 may include delivery orifice 232. Orifice 232 may be in fluid communication with bore 236.

Figure 3:
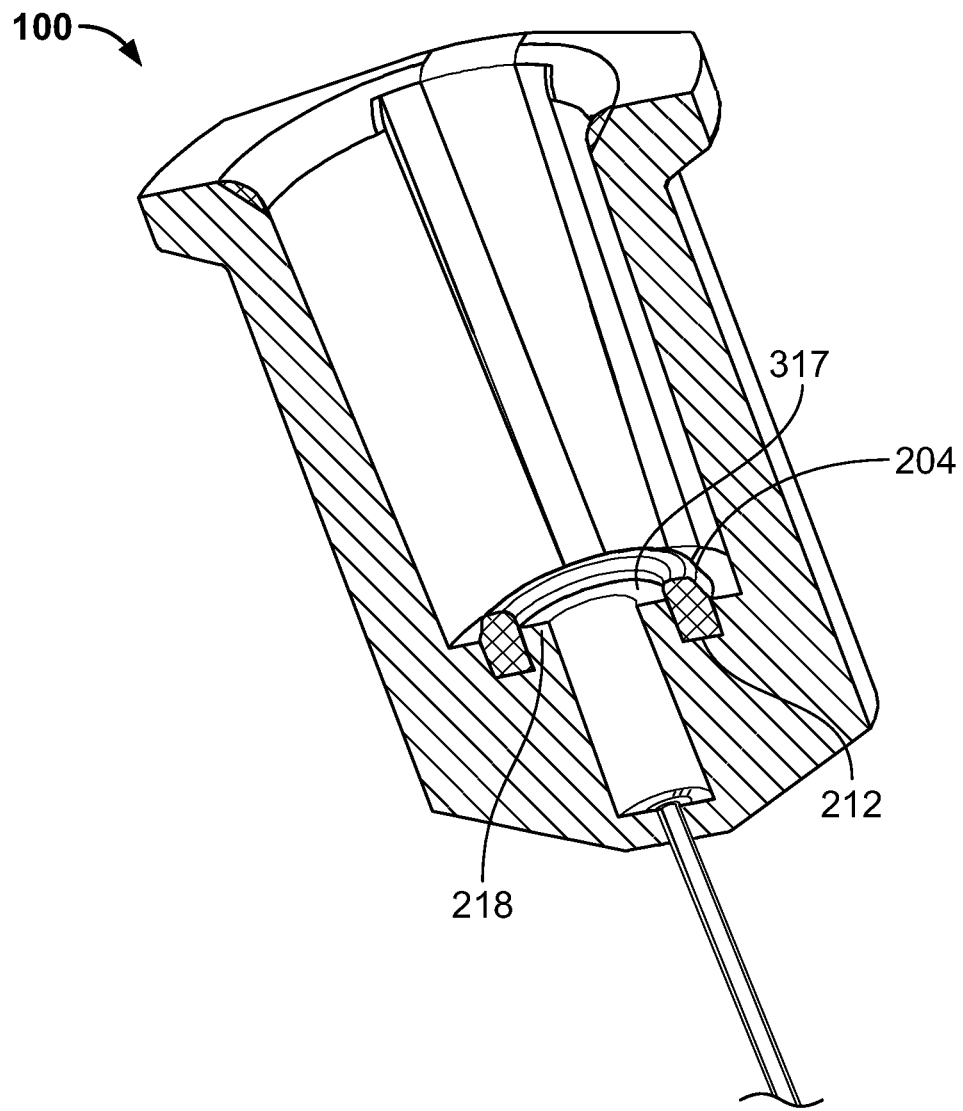
FIG. 3 is a partial cross-sectional view of the apparatus shown in FIG. 1, the view taken along lines 3-3 (shown in FIG. 1)

FIG. 3 is a cross-sectional view taken along lines 3-3 (shown in FIG. 1). FIG. 3 shows that gasket 204 may be seated in recess 212. Gasket 204 may circumscribe detent 218. Detent 218 may include detent top 317. Gasket 204 may extend longitudinally from recess 212 in a proximal direction beyond top 317.

Figure 4:
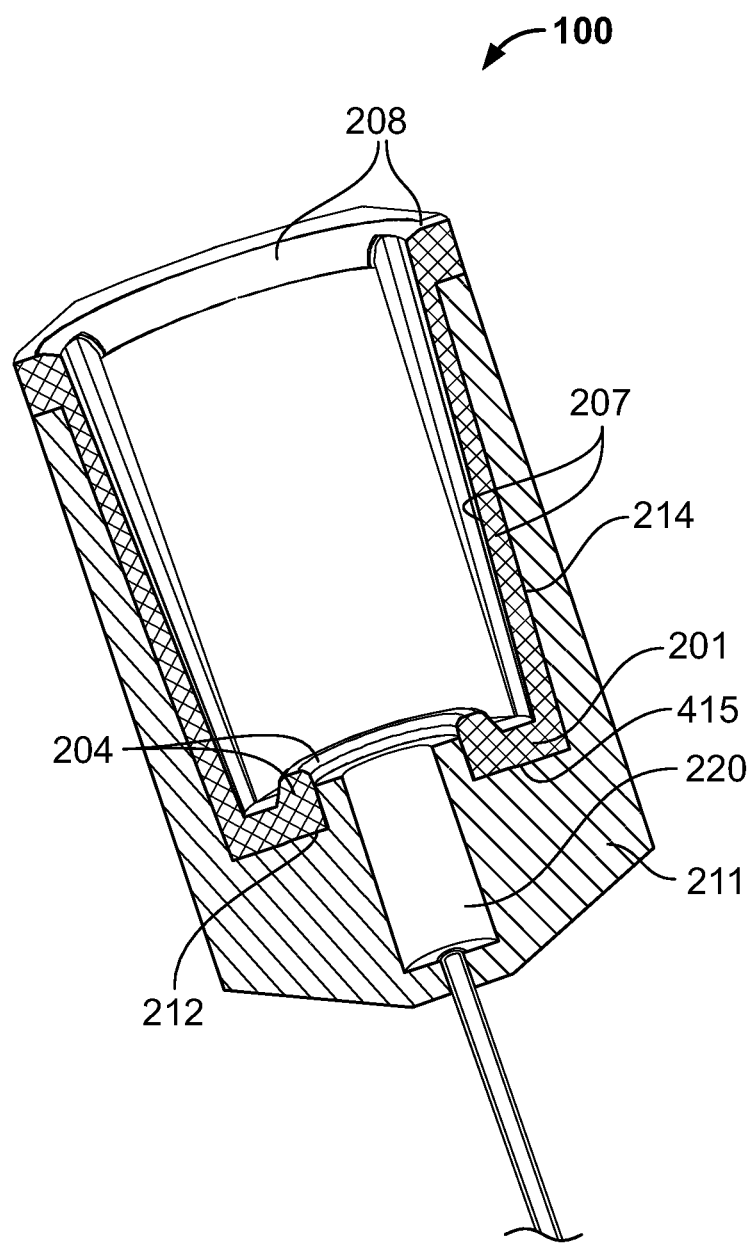
FIG. 4 is a partial cross-sectional view of the apparatus shown in FIG. 1, the view taken along lines 4-4 (shown in FIG. 1)

FIG. 4 is a cross-sectional view taken along lines 4-4 (shown in FIG. 1). FIG. 4 shows that body 211 may include transverse recess 415. Recess 415 may be continuous with recess 212. Recess 415 may be continuous with recess 214.

FIG. 4 shows that gasket 204 may be seated in recess 212. Gasket 204 may be connected to member 201. Member 201 may be seated in recess 415. Member 201 may be connected to member 207. Member 207 may be seated in recess 214. Member 207 may be connected to rim 208.

Figure 5:
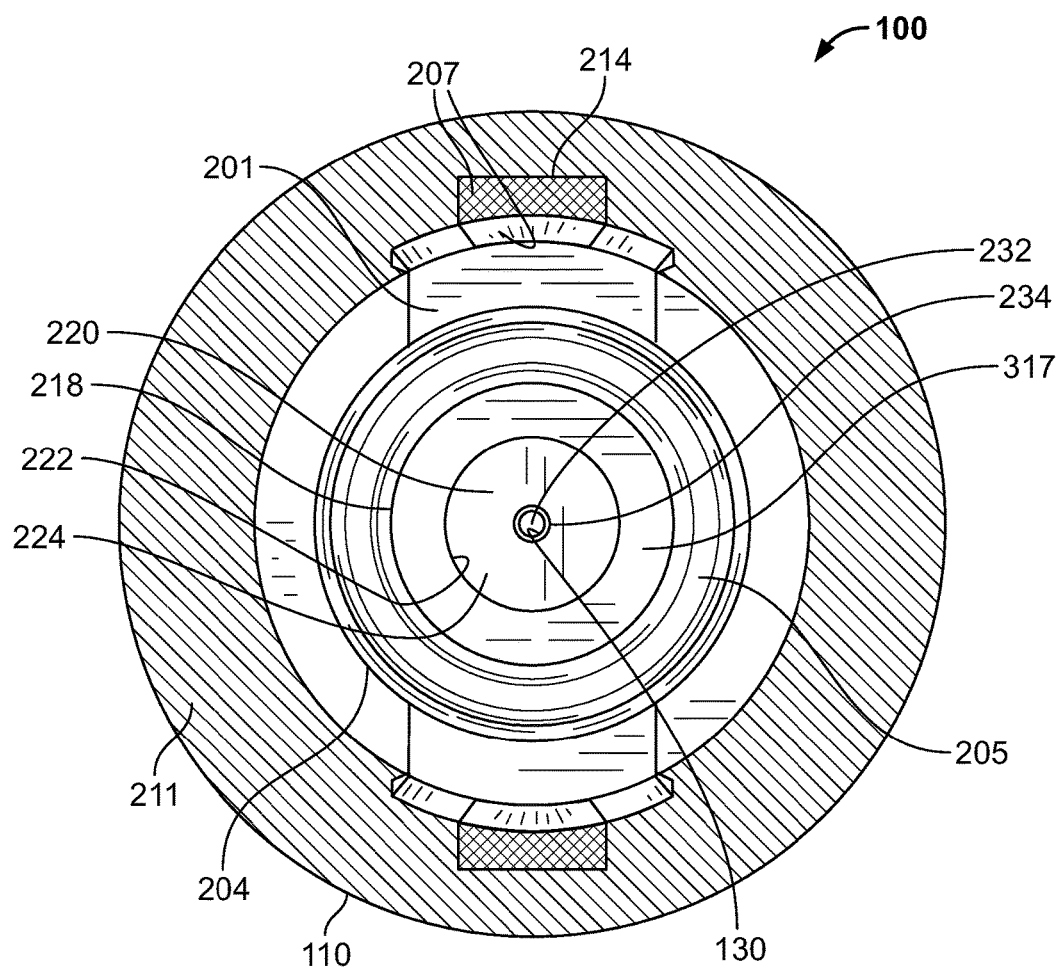
FIG. 5 is a partial cross-sectional view of the apparatus shown in FIG. 1, the view taken along lines 5-5 (shown in FIG. 1)

FIG. 5 is a cross-sectional view taken along lines 5-5 (shown in FIG. 1). FIG. 5 shows that gasket 204 may be seated within fitting 110.

Orifice 232 may be distal-most in this view. Orifice 232 may be at a distal end of needle 130. Needle 130 may be in fluid communication with inlet 234. Floor 224 may define inlet 234. Floor 224 may be the distal boundary of void 220. Floor 224 may be distal to opening 222. Void 220 may be in fluid communication with opening 222. Detent 218 may circumscribe opening 222. Gasket 204 may circumscribe detent 218. Gasket 204 may connect to member 201. Member 201 may connect to member 207. Member 201 may be distal to member 207. Member 207 may be seated in recess 214.

In this view, member 201 may be distal to top 317. Top 317 may be distal to face 205.

Figure 6:
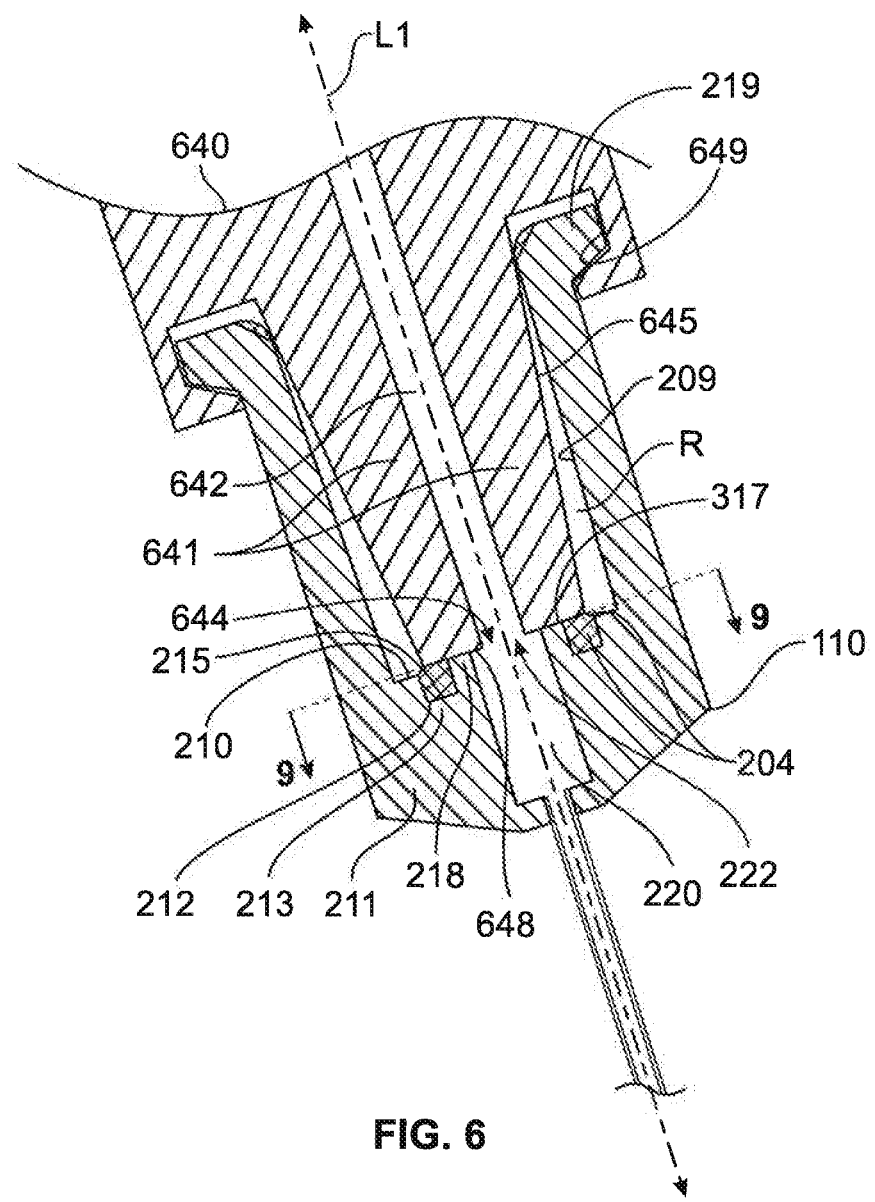
FIG. 6 is a cross-sectional view (similar to that of FIG. 3) of the apparatus shown in FIG. 1, along with other apparatus.

FIG. 6 shows fitting 110, in a view such as that along lines 3-3 (shown in FIG. 1), with dispenser distal end 641 of dispenser 640 inserted into fitting 110.

Dispenser 640 may define longitudinal dispenser axis $L_1$. End 641 may include lateral wall 645. End 641 may include terminal surface 648. Surface 648 may define dispenser aperture 644. Aperture 644 may be a distal-most end of dispenser bore 642. Bore 642 may be parallel to axis $L_1$. Bore 642 may be configured to contain a fluid to be dispensed. Bore 642 may be in fluid communication with aperture 644.

Dispenser 640 may be received by fitting 110. End 641 may be longitudinally inserted into fitting 110. When end 641 is inserted into fitting 110, axis $L_1$ may be collinear with axis L (shown in FIG. 1). Insertion of end 641 into fitting 110 may be limited by the lodging of surface 648 against detent 218. When surface 648 lodges against detent 218, surface 648 may lodge against top 317. When surface 648 lodges against detent 218, aperture 644 may be in fluid communication with opening 222.

When surface 648 lodges against detent 218, gasket 204 may be compressed between surface 648 and base portion 213. When gasket 204 is compressed between surface 648 and base portion 213, gasket 204 may be compressed between surface 648 and distal bottom 215 of recess. When gasket 204 is compressed between surface 648 and base portion 213, gasket 204 may be in sealing contact with surface 648. When gasket 204 is in sealing contact with surface 648, seal 204, wall 645, facet 210 and wall 209 may define region R. When gasket 204 is in sealing contact with surface 648, region R may be isolated from fluid communication with bore 642.

Dispenser 640 may include engagement surface 649. When end 641 is inserted into fitting 110, member 219 may engage surface 649. Engagement of member 219 and surface 649 may maintain gasket 204 in sealing contact with surface 648.

Figure 7:
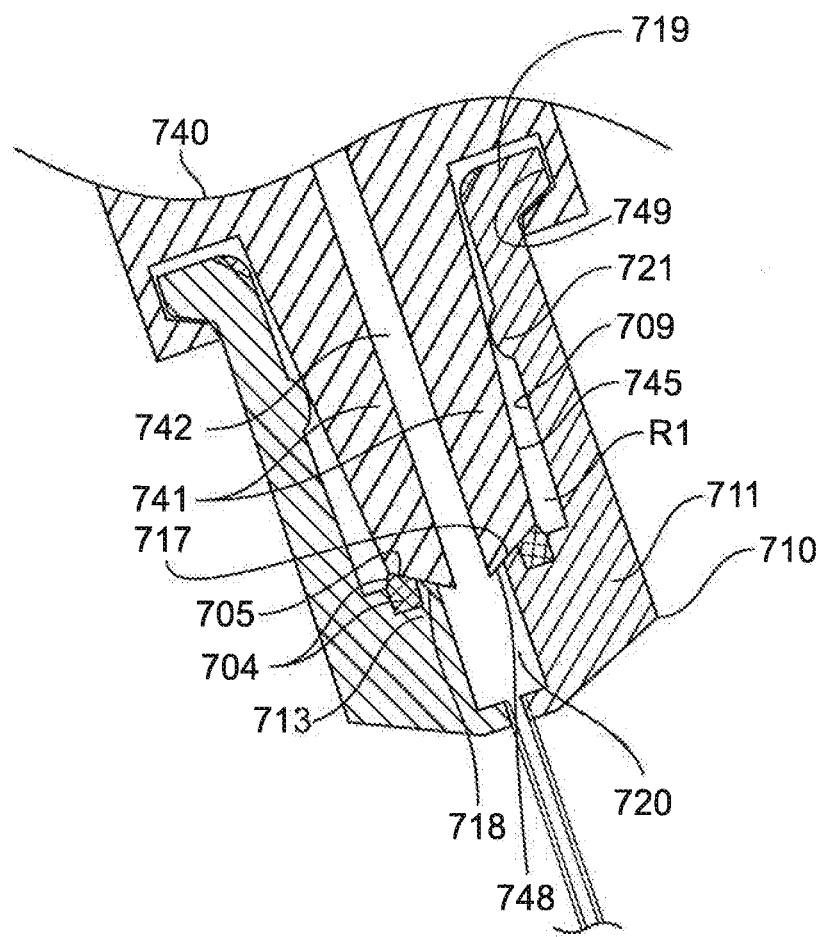
FIG. 7 is a cross-sectional view of apparatus in accordance with the principles of the invention, along with other apparatus.

FIG. 7 shows illustrative fitting 710, in a view similar to that of fitting 110 shown in FIG. 4, with dispenser distal end 741 of dispenser 740 inserted into fitting 710. Fitting 710 may have one or more features in common with fitting 110 (shown in FIG. 1).

Fitting 710 may include body 711. Body 711 may include interior wall 709. Body 711 may include void 720.

Body 711 may include base portion 713. Base portion 713 may support seal 704. Seal 704 may include contoured top 705. Base portion 713 may support detent 718. Detent 718 may include contoured face 717.

Dispenser 740 may include lateral wall 745. Dispenser 740 may include bore 742. Bore 742 may be configured to contain fluid to be dispensed. Dispenser 740 may include contoured terminal surface 748. Surface 748 may be complementary to top 705. Surface 748 may be complementary to face 717.

FIG. 7 shows that dispenser 740 may be inserted into fitting 710. Insertion of dispenser 740 into fitting 710 may be limited by the lodging of surface 748 against detent 718. When surface 748 lodges against detent 718, bore 742 may be in fluid communication with void 720.

When surface 748 lodges against detent 718, gasket 704 may be compressed between surface 748 and base portion 713. When gasket 704 is compressed between surface 748 and base portion 713, gasket 704 may be in sealing contact with surface 748. When gasket 704 is in sealing contact with surface 748, seal 704, wall 745 and wall 709 may define region R1. When gasket 704 is in sealing contact with surface 748, region R1 may be isolated from fluid communication with bore 742.

Fitting 710 may include engagement member 719. Dispenser 740 may include engagement surface 749. When dispenser 740 is inserted into fitting 710, member 719 may engage surface 749. Engagement of member 719 and surface 749 may maintain gasket 704 in sealing contact with surface 748.

Body 711 may include one or more bosses. For example, body 711 may include boss 721. When dispenser 740 is inserted into fitting 710, boss 721 may engage wall 745. Engagement of boss 721 and wall 745 may maintain gasket 704 in sealing contact with surface 748.

Figure 8:
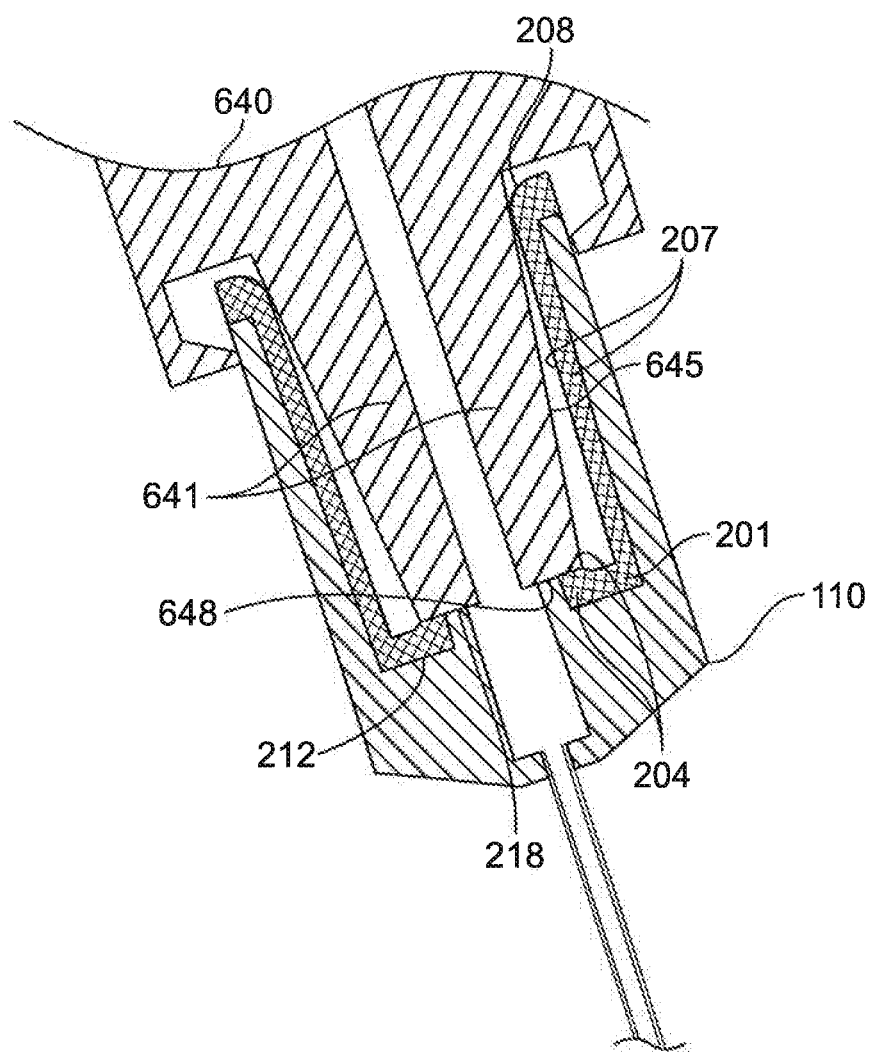
FIG. 8 is a cross-sectional view (similar to that of FIG. 4) of the apparatus shown in FIG. 1, along with other apparatus.

FIG. 8 shows fitting 110 in a sectional view taken along lines 4-4 (shown in FIG. 1).

FIG. 8 shows fitting 110, in a view such as that along lines 4-4 (shown in FIG. 1), with dispenser distal end 641 of dispenser 640 inserted into fitting 110.

When dispenser 640 is inserted into fitting 110, surface 648 may lodge against detent 218. The lodging of surface 648 against detent 218 may compress gasket 204. When gasket 204 is compressed, gasket 204 may sealingly contact surface 648.

When dispenser 640 is inserted into fitting 110, wall 645 may engage rim 208. Engagement of rim 208 and wall 645 may align axis $L_1$ (shown in FIG. 6) with axis L (shown in FIG. 1).

Engagement of rim 208 and wall 645 may deform rim 208. When rim 208 is deformed by dispenser 640 and when gasket 204 is compressed by dispenser 640, tensional forces may be transmitted between rim 208 and gasket 204. The tensional forces may be transmitted through member 201 and member 207. The tensional forces may strengthen the sealing contact of gasket 204 with surface 648 by further urging gasket 204 against surface 648. The tensional forces may strengthen the engagement of rim 208 and wall 645 by wedging rim 208 further into the gap between rim 208 and wall 645.

Figure 9:
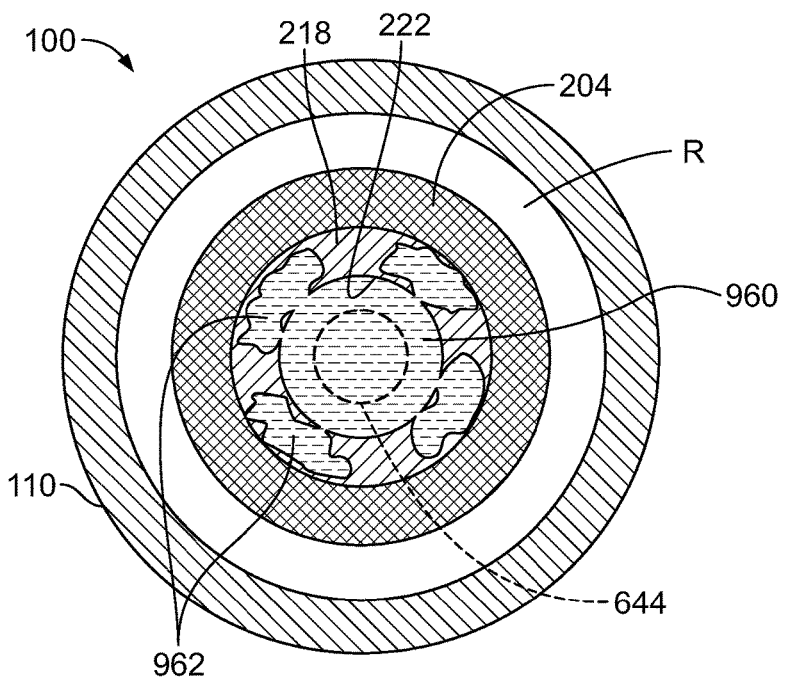
FIG. 9 is a cross-sectional view of the apparatus, along with other apparatus, shown in FIG. 6, the view taken along lines 9-9 (shown in FIG. 6)

FIG. 9 is a cross-sectional view of fitting 110 with dispenser 640 (shown in FIG. 6) inserted into fitting 110, taken along lines 9-9 (shown in FIG. 6). Lines 9-9 may lie in a plane of abutment of surface 648 (shown in FIG. 6) against detent 218 and against gasket 204. Detent 218, gasket 204 and region R may lie within fitting 110.

Fluid 960 may span aperture 644. Fluid 960 may span opening 222. Fluid 960 may be the fluid that bore 642 (shown in FIG. 6) may be configured to contain.

One or more volumes of fluid may lie within an inner border of gasket 204. For example, volume 962 may lie within the inner border of gasket 204. Volume 962 may lie upon detent 218. Volume 962 may lie below surface 648 (shown in FIG. 6). Volume 962 may be contiguous with fluid 960 spanning aperture 644. Fluid in volume 962 may be fluid 960. When gasket 204 is in sealing contact with surface 648 (shown in FIG. 6), the fluid in volume 962 may be sealingly isolated from region R. When gasket 204 is in sealing contact with surface 648 (shown in FIG. 6), aperture 644 may be sealingly isolated from region R. When gasket 204 is in sealing contact with surface 648 (shown in FIG. 6), opening 222 may be sealingly isolated from region R.

Figure 10:
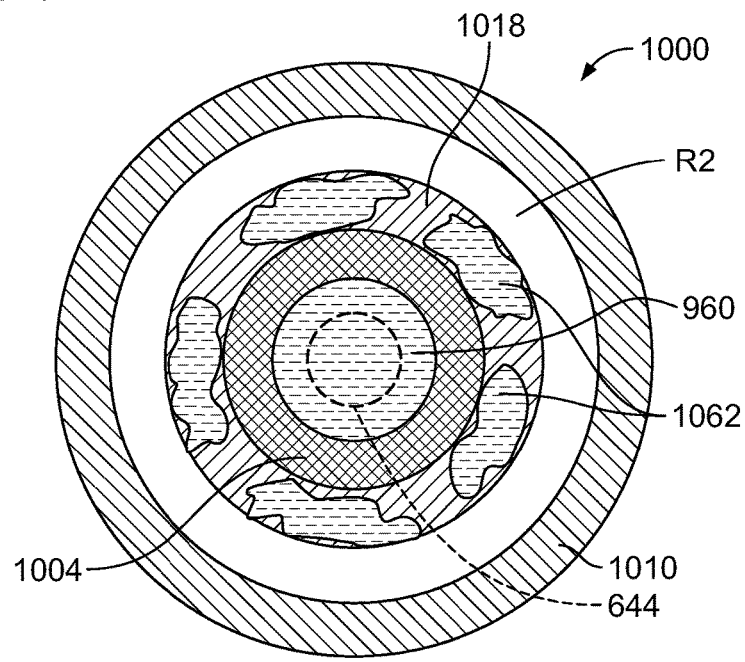
FIG. 10 is a cross-sectional view (similar to that of FIG. 9) of apparatus in accordance with the principles of the invention, along with other apparatus.

FIG. 10 shows illustrative device 1000. Device 1000 may have one or more features in common with fitting 110, with dispenser 640 (shown in FIG. 6) inserted into fitting 110, as shown in FIG. 9. In FIG. 9, detent 218, gasket 204 and region R may lie within fitting 110; in device 1000, detent 1018, gasket 1004 and region R2 may lie within fitting 1110. In FIG. 9, syringe terminal surface 648 (shown in FIG. 6) may abut detent 218 and sealingly engage gasket 204; in device 1000, a syringe terminal surface (not shown) may abut detent 1018 and sealingly engage gasket 1004. In FIG. 9, fluid 960 may span aperture 644; in device 1000, fluid 960 may span an aperture of the syringe terminal surface (not shown).

Device 1000 may differ from fitting 110, with dispenser 640 (shown in FIG. 6) inserted into fitting 110, as shown in FIG. 9. In FIG. 9, an outer annular border of detent 218 may lie within an inner annular border of gasket 204; in device 1000, an outer annular border of gasket 1004 may lie within an inner annular border of detent 1018. In FIG. 9, fluid 960 may be bordered by an inner annular border of detent 218; in device 1000, fluid 960 may be bordered by an inner annular border of seal 1004.

One or more volumes of fluid may lie outside the outer annular border of gasket 1004. For example, volume 1062 may lie outside the outer annular border of gasket 1004. Volume 1062 may lie upon detent 1018. Volume 1062 may lie below the terminal syringe surface (not shown) of device 1000. When gasket 1004 is in sealing contact with the terminal syringe surface (not shown) of device 1000, the fluid in volume 1062 may be sealingly isolated from the fluid-spanned open center of device 1000. When gasket 1004 is in sealing contact with the terminal syringe surface (not shown) of device 1000, the open center of device 1000 may be sealingly isolated from region R2.

Figures 11, 12:
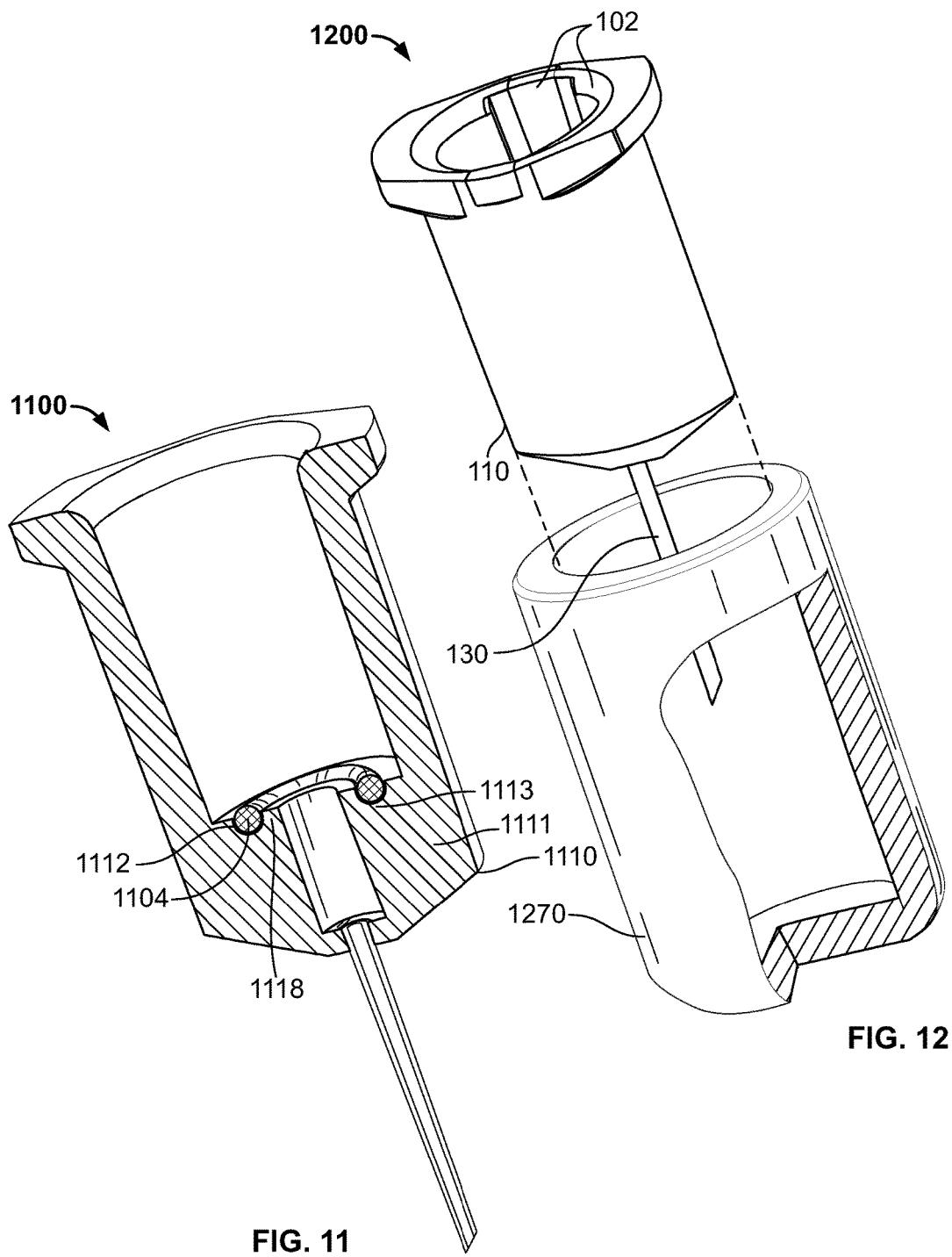
FIG. 11 is a partial cross-sectional view of apparatus in accordance with the principles of the invention.
FIG. 12 is a perspective view of the apparatus shown in FIG. 1, along with other apparatus, including a partial cross-sectional view of the other apparatus.

FIG. 11 shows illustrative device 1100. Device 1100 may have one or more features in common with device 100 (shown in FIG. 1).

Device 1100 may include fitting 1110. Fitting 1110 may include body 1111. Body 1111 may include body portion 1113. Body portion 1113 may support detent 1118.

Body portion 1113 may include recess 1112. Recess 1112 may receive seal 1104. A cross-section of recess 1112 may be complementary to a cross-section of seal 1104. Body portion 1113 may support seal 1104.

Seal 1104 may be press-fit into recess 1112. Seal 1104 may adhere to a surface of recess 1112.

Fitting 1110 may receive dispenser 640 (shown in FIG. 6). When received by fitting 1110, dispenser 640 may abut detent 1118 and sealingly engage seal 1104.

FIG. 12 shows illustrative device 1200. Device 1200 may include fitting 110. Fitting 110 may receive insert 102. Fitting 110 may support needle 130. Fitting 110 may define longitudinal axis L (shown in FIG. 1).

Device 1200 may include needle guard 1270. Guard 1270 may engage fitting 110. Fitting 110 may be longitudinally inserted into engagement with guard 1270. Fitting 110 may be twisted into engagement with guard 1270. Engagement of fitting 110 with guard 1270 may allow a dispenser, such as dispenser 640 (shown in FIG. 6), to be engaged with fitting 110 with no shifting of fitting 110 relative to guard 1270.

Fitting 110 may be stored engaged with guard 1270. Guard 1270 may axially surround needle 130. Guard 1270 may cover a sharp distal end of needle 130. Engagement of fitting 110 with guard 1270 may allow a practitioner to engage a dispenser with fitting 110 while needle 130 is axially surrounded by guard 1270.

Guard 1270 may be removed prior to adjustment of dispenser fluid volume.

Figure 13:
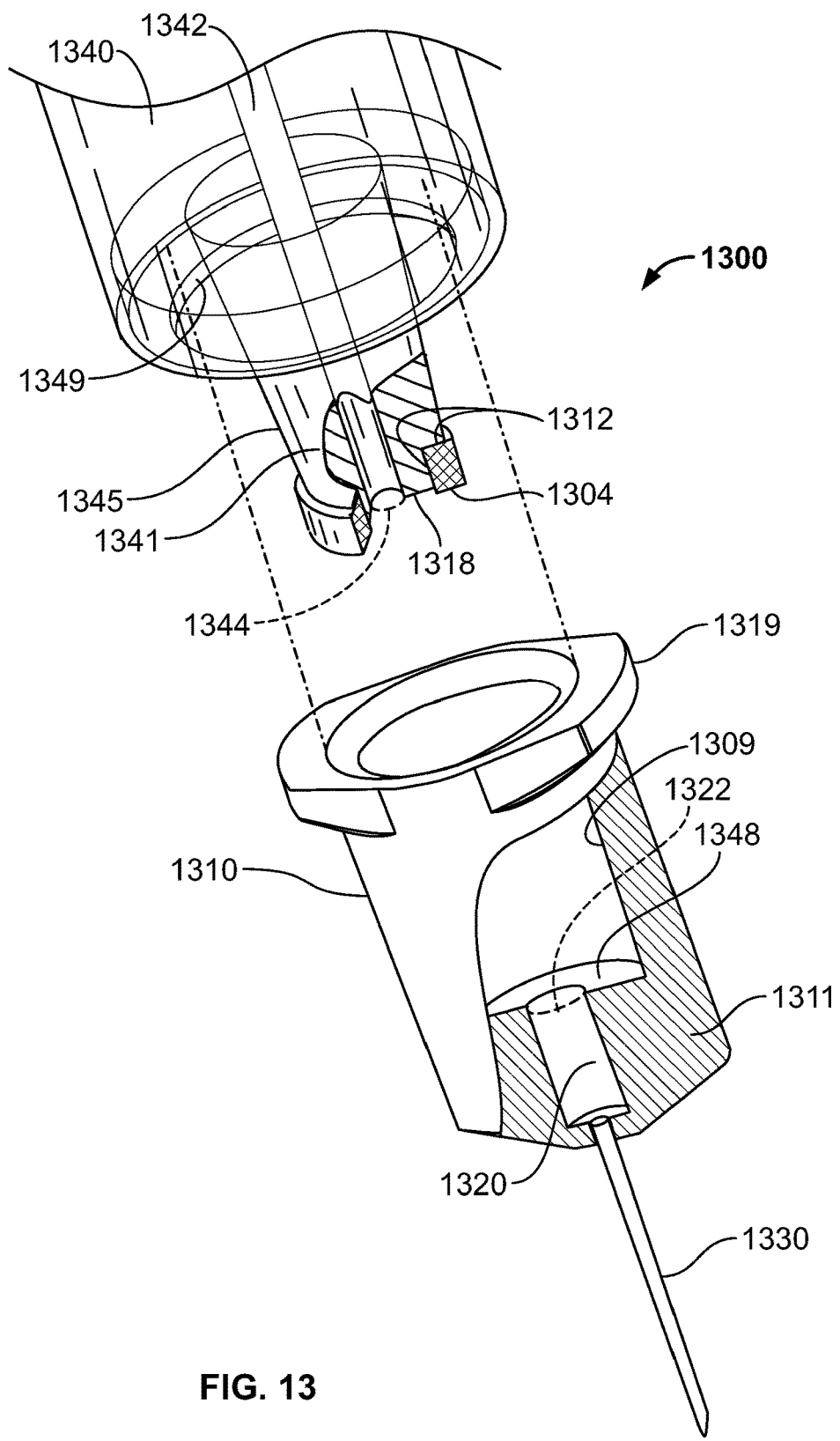
FIG. 13 is an exploded perspective view of apparatus in accordance with the principles of the invention including partial cross-sectional views of the apparatus.

FIG. 13 shows illustrative device 1300. Device 1300 may have one or more features in common with fitting 110, with dispenser 640 inserted into fitting 110, as shown in FIG. 6.

Device 1300 may include dispenser 1340. Device 1300 may include fitting 1310. Fitting 1300 may be configured to receive a portion of dispenser 1340.

Dispenser 1340 may include dispenser bore 1342. Bore 1342 may be configured to contain a fluid to be dispensed. Dispenser 1340 may include distal end 1341. End 1341 may include lateral wall 1345.

End 1341 may support detent 1318. Detent 1318 may circumscribe dispenser aperture 1344. Aperture 1344 may be a distal-most end of bore 1342. Bore 1342 may be in fluid communication with aperture 1344. Dispenser 1340 may include engagement surface 1349.

End 1341 may support gasket 1304. End 1341 may include recess 1312. Recess 1312 may be configured to receive gasket 1304. Recess 1312 may be annular. Gasket 1304 may be annular. Gasket 1304 may snugly engage recess 1312. Gasket 1304 may circumscribe detent 1318.

Detent 1318 may include dispenser aperture 1344. Aperture 1344 may be a distal-most end of bore 1342. Bore 1342 may be in fluid communication with aperture 1344. An inner annular border of detent 1318 may be in fluid communication with bore 1342.

Dispenser 1340 may include engagement surface 1349.

Fitting 1310 may include fitting body 1311. Body 1311 may support needle 1330.

Body 1311 may include proximal surface 1348. Surface 1348 may define opening 1322. Body 1311 may include void 1320. Opening 1322 may be in fluid communication with void 1320. Void 1320 may be in fluid communication with needle 1330.

Fitting 1310 may include interior wall 1309. Fitting 1310 may include engagement member 1319.

Figure 14:
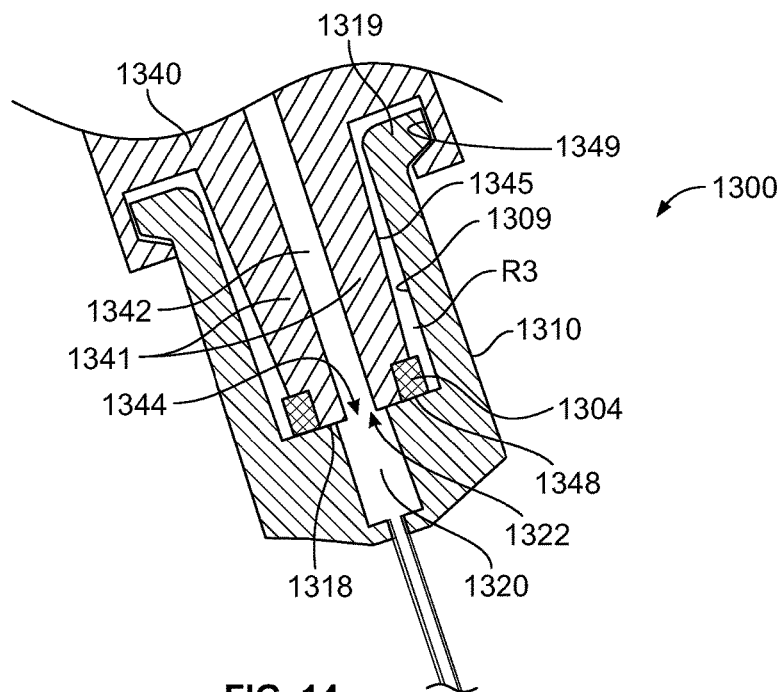
FIG. 14 is a cross-sectional view of the apparatus shown in FIG. 13.

FIG. 14 shows device 1300. FIG. 14 shows that end 1341 may be inserted into fitting 1310. Insertion of end 1341 into fitting 1310 may be limited by the lodging of detent 1318 against surface 1348. When detent 1318 lodges against surface 1348, aperture 1344 may be in fluid communication with opening 1322.

When detent 1318 lodges against surface 1348, gasket 1304 may be deformed into sealing contact with surface 1348. When gasket 1304 is in sealing contact with surface 1348, gasket 1304, wall 1345 and wall 1309 may define region R3. When gasket 1304 is in sealing contact with surface 1348, region R3 may be isolated from fluid communication with bore 1342.

When end 1341 is inserted into fitting 1310, member 1319 may engage surface 1349. Engagement of member 1319 and surface 1349 may maintain gasket 1304 in sealing contact with surface 1348.

Figure 15:
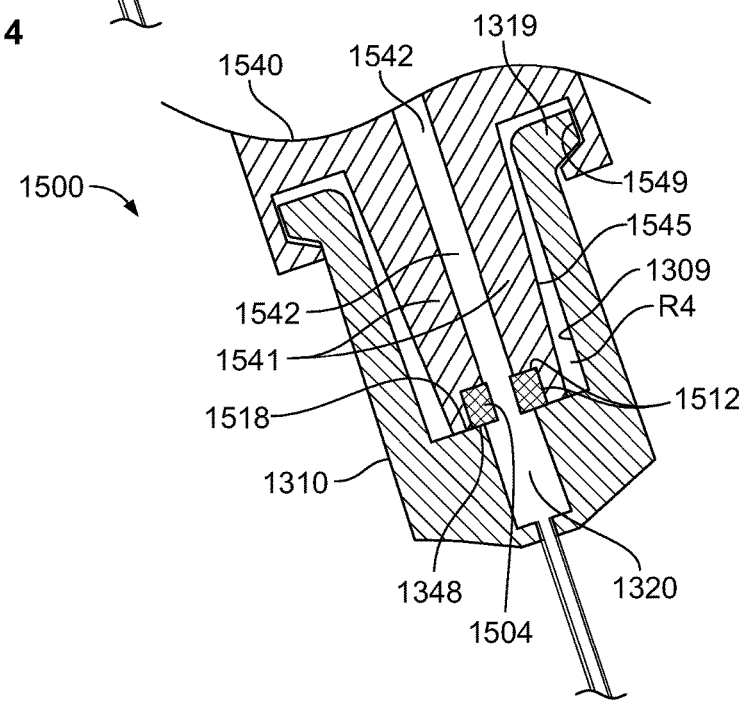
FIG. 15 is a cross-sectional view (similar to that of FIG. 14) of apparatus in accordance with the principles of the invention.

FIG. 15 shows illustrative device 1500. Device 1500 may have one or more features in common with device 1300 (shown in FIG. 13).

Device 1500 may include fitting 1310. Device 1500 may include dispenser 1540. Dispenser 1540 may have one or more features in common with dispenser 1340 (shown in FIG. 14). Dispenser 1540 may be inserted into fitting 1310.

Dispenser 1540 may include dispenser bore 1542. Bore 5342 may be configured to contain a fluid to be dispensed.

Dispenser 1540 may include distal end 1541. End 1541 may include lateral wall 1545.

End 1541 may support detent 1518. Detent 1518 may circumscribe gasket 1304.

End 1541 may support gasket 1504. End 1541 may define recess 1512. Recess 1512 may be configured to receive gasket 1504. Recess 1512 may be annular. Gasket 1504 may be annular. Gasket 1504 may snugly engage recess 1512. An inner annular border of gasket 1504 may be in fluid communication with bore 1542.

Dispenser 1540 may include engagement surface 1549.

Insertion of dispenser end 1541 into fitting 1310 may be limited by the lodging of detent 1518 against surface 1348. When detent 1518 lodges against surface 1348, bore 1542 may be in fluid communication with void 1320.

When detent 1518 lodges against surface 1348, gasket 1504 may be deformed into sealing contact with surface 1348. When gasket 1504 is in sealing contact with surface 1348, gasket 1504, wall 1545 and wall 1309 may define region R4. When gasket 1504 is in sealing contact with surface 1348, region R4 may be isolated from fluid communication with bore 1542.

When end 1541 is inserted into fitting 1310, member 1319 may engage surface 1549. Engagement of member 1319 and surface 1549 may maintain gasket 1504 in sealing contact with surface 1348.

Figure 16:
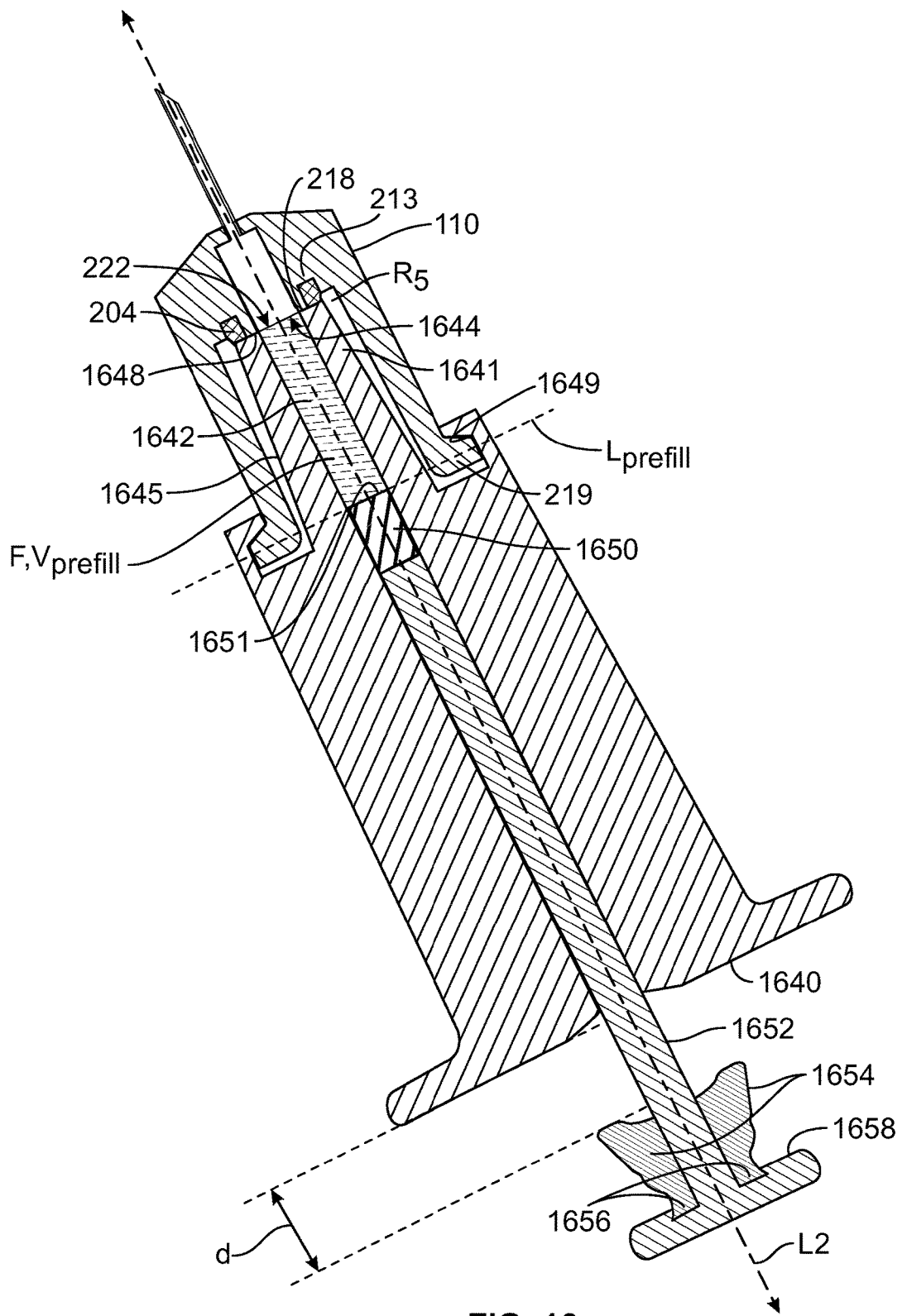
FIG. 16 is a cross-sectional view of apparatus in accordance with the principles of the invention.
Figure 17:
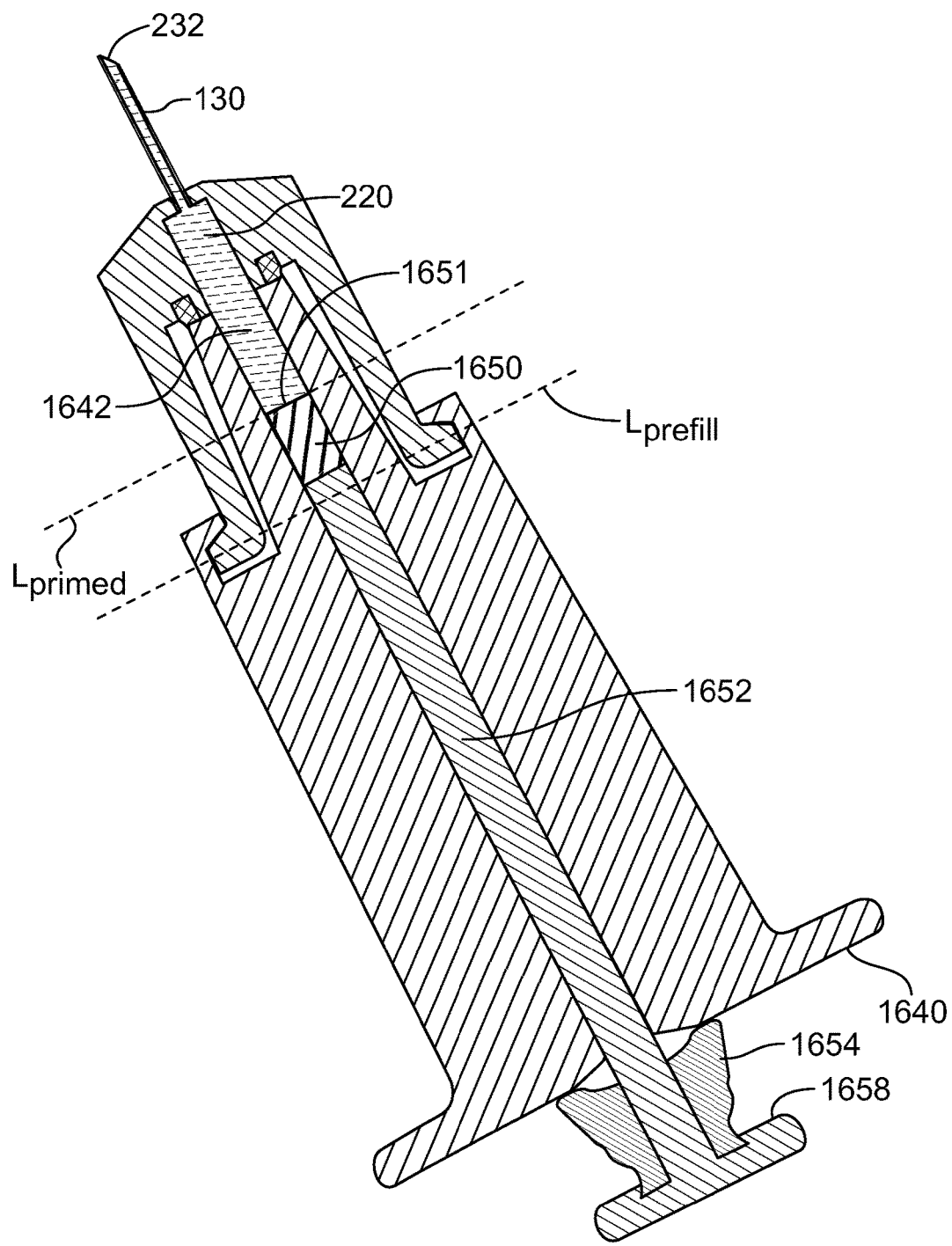
FIG. 17 is another cross-sectional view of the apparatus shown in FIG. 16.
Figure 18:
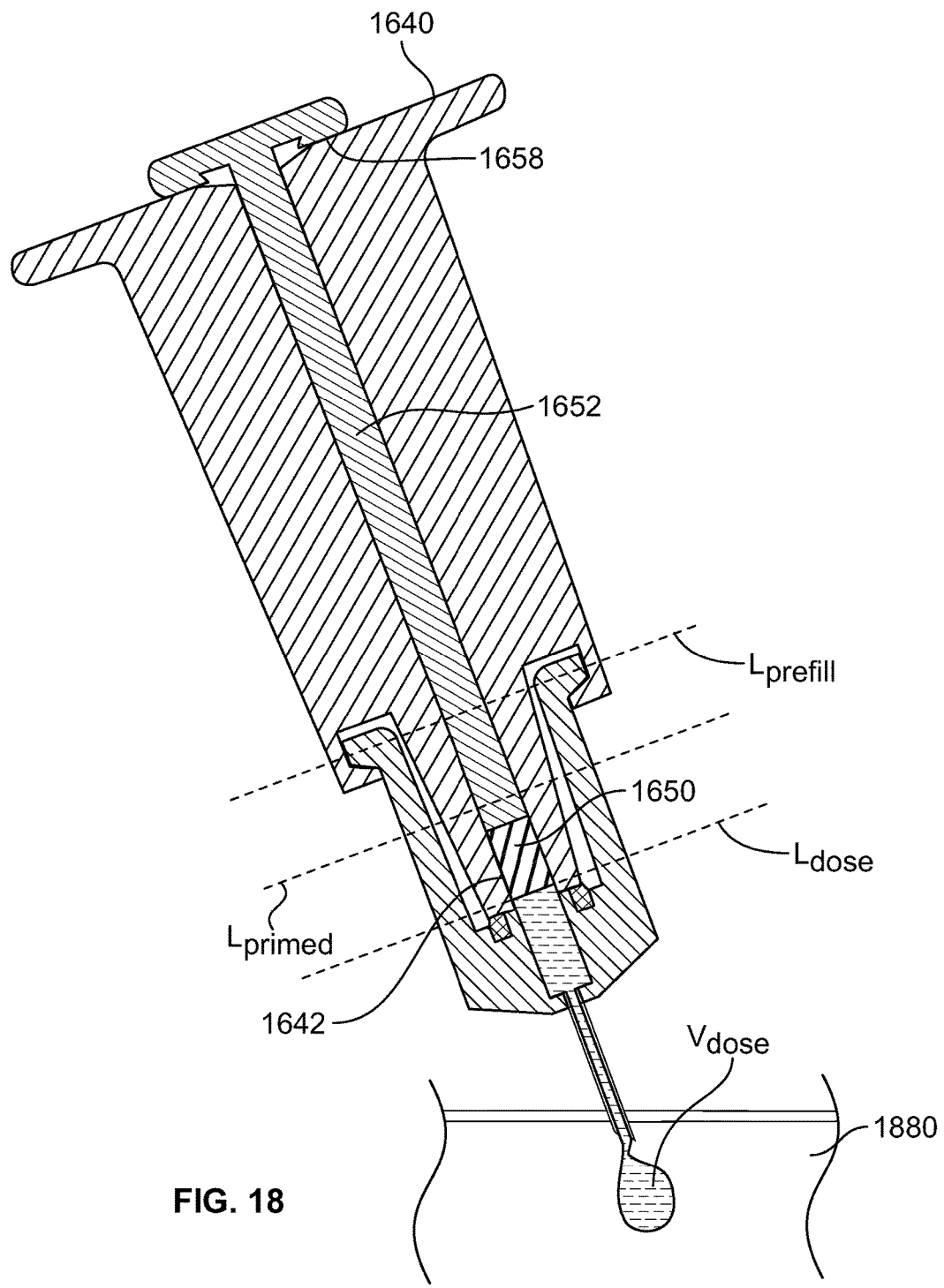
FIG. 18 is another cross-sectional view of the apparatus shown in FIG. 17.

FIGS. 16, 17 and 18 show fitting 110 with distal end 1641 of dispenser 1640 inserted into fitting 110. Dispenser 1640 may have one or more features in common with dispenser 640 (shown in FIG. 6).

Dispenser 1640 may define longitudinal dispenser axis $L_2$. End 1641 may include lateral wall 1645. End 1641 may include terminal surface 1648. Surface 1648 may define dispenser aperture 1644. Aperture 1644 may be a distal-most end of dispenser bore 1642. Bore 1642 may be parallel to axis $L_2$. Bore 1642 may be configured to contain a fluid F to be dispensed. Fluid F may include a medicament. Bore 1642 may be in fluid communication with aperture 1644.

Dispenser 1640 may include plunger shaft 1652. Shaft 1652 may extend proximally out of a proximal-most end of bore 1642. Shaft 1652 may include shaft stop 1658. Stop 1658 may be a distal face of a proximal transverse surface of shaft 1652. Shaft 1652 may connect with shaft collar 1654. Grooves 1656 may maintain the connection of shaft 1652 and collar 1654. Collar 1654 may be removed from shaft 1652 by shifting collar 1654 out of grooves 1656.

Shaft 1652 may support plunger plug 1650. Longitudinally moving shaft 1652 within bore 1642 may slide plug 1650 within bore 1642. Plug 1650 may slideably seal bore 1642. When shaft 1652 is distally depressed, plug 1650 may drive fluid F distally within bore 1642.

Dispenser 1640 may be received by fitting 110. When end 1641 is inserted into fitting 110, axis $L_2$ may be collinear with axis L (shown in FIG. 1). Insertion of end 1641 into fitting 110 may be limited by the lodging of surface 1648 against detent 218. When surface 1648 lodges against detent 218, aperture 1644 may be in fluid communication with opening 222.

When surface 1648 lodges against detent 218, gasket 204 may be compressed between surface 1648 and base portion 213. When gasket 204 is compressed between surface 1648 and base portion 213, gasket 204 may be in sealing contact with surface 1648. When gasket 204 is in sealing contact with surface 1648, seal 204, wall 1645 and wall 209 may define region R5. When gasket 204 is in sealing contact with surface 648, region R5 may be isolated from fluid communication with bore 1642.

Dispenser 1640 may include engagement surface 1649. When end 1641 is inserted into fitting 110, member 219 may engage surface 1649. Engagement of member 219 and surface 1649 may maintain gasket 204 in sealing contact with surface 1648.

Volume $V_{prefill}$ of fluid F may be present in bore 1642. The volume may be contained between aperture 1644 and distal surface 1651 of plug 1650. $V_{prefill}$ may be an initial volume of fluid F in dispenser 1640. Dispenser 1640 may be pre-filled with $V_{prefill}$ of fluid F. Pre-filling dispenser 1640 may set distal surface 1651 of plug 1650 at location $L_{prefill}$ within dispenser 1640. When surface 1651 is at $L_{prefill}$, a distance between a proximal-most surface of dispenser 1640 and a distal-most surface of collar 1654 may be distance d.

FIG. 17 shows distal surface 1651 of plug 1650 at location $L_{primed}$. $L_{primed}$ may be distal along axis $L_2$ (shown in FIG. 16) relative to location $L_{prefill}$. Plug 1650 may be moved to $L_{primed}$ by depressing shaft 1652 distally into bore 1642 as far as collar 1654 allows. Shaft 1652 may be depressed distally by distance d (shown in FIG. 16). When shaft 1652 is depressed distally by distance d, the distal-most surface of collar 1654 may contact the proximal-most surface of dispenser 1640.

Depressing plug 1650 from $L_{prefill}$ to $L_{prefill}$ may distally drive a portion of $V_{prefill}$ out of bore 1642. That portion may be a volume $V_{primed}$. Part of $V_{primed}$ may be advanced distally into void 220. Part of $V_{primed}$ may be advanced distally into needle 130. Part of $V_{primed}$ may be advanced to orifice 232. The volume of fluid remaining within bore 1642 may be given by the difference $V_{prefill}$ minus $V_{primed}$. The difference $V_{prefill}$ minus $V_{primed}$ may include a dose volume $V_{dose}$.

FIG. 18 shows that dose volume $V_{dose}$ may be dispensed into target 1880. $V_{dose}$ may be dispensed into target 1880 by advancing plug 1650 within bore 1642 from $L_{primed}$ to location $L_{dose}$. $L_{dose}$ may be distal to $L_{primed}$. Plug 1650 may be advanced to $L_{dose}$ by depressing shaft 1652, after removal of collar 1654, distally into bore 1642 as far as allowed by shaft stop 1658. When shaft 1652, after removal of collar 1654, is fully depressed into bore 1642, stop 1658 may contact the proximal-most surface of dispenser 1640.

The difference $L_{primed}$ minus $L_{dose}$ may correspond to a maximum delivery stroke of dispenser 1640. The difference $L_{prefill}$ minus $L_{dose}$ may correspond to the maximum stroke length of shaft 1652. The maximum stroke length of shaft 1652 may be set so as to leave a predetermined volume of fluid F within bore 1642 after full depression of shaft 1652 into bore 1642.

Figure 19:
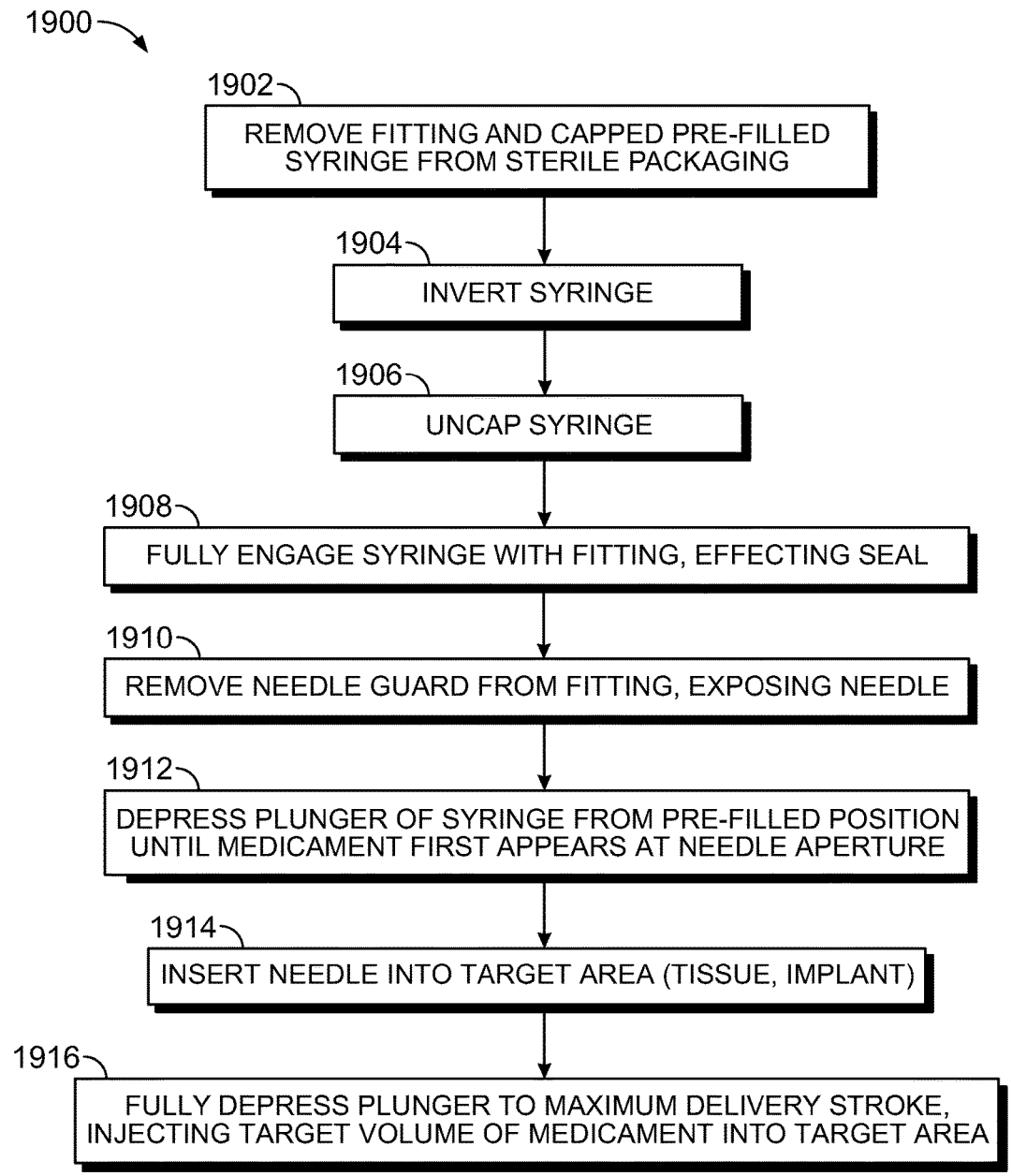
FIG. 19 shows an illustrative process in accordance with the principles of the invention.

Processes in accordance with the principles of the invention may include one or more features of the processes illustrated in FIG. 19. One or more steps of the processes may be performed with all or portions of the apparatus shown in FIGS. 1-18.

Some steps of the process may be performed by a practitioner, while other steps may be performed by others. For simplicity of presentation, the steps of the process are presented performed by a "user."

The process may be a therapeutic process. The therapeutic process may include injection of the medicament into a patient. A target volume of the medicament may be injected into a target tissue of a patient. The target volume of the medicament may be injected into an implant. The implant may be implanted in the patient. The target volume may be a dose volume called for in the therapeutic process.

FIG. 19 shows illustrative steps of process 1900 for delivering a low volume of fluid. Components of the apparatus may be packaged in sterile packaging. The pre-filled syringe and the fitting may be packaged as separate apparatus components. The fitting may be engaged with the needle guard.

A volume of fluid pre-filling the syringe may be greater than the low volume to be delivered. The volume of fluid pre-filling the syringe may be large enough to be set with more precision than may be possible were the syringe to be pre-filled with the low volume to be delivered. The pre-filled syringe may be capped on the distal end by a removable cap. The cap may prevent loss of fluid by leakage during storage of the syringe. A volume of fluid containing the medicament to be delivered may fill the syringe from the distal surface of the plunger plug to an inner surface of the cap.

The pre-filled syringe may have its shaft positioned such that the distal surface of the plunger plug is at $L_{prefill}$ (shown in FIG. 16). The shaft collar may be connected to the proximal end of the syringe shaft (shown in FIG. 16).

Process 1900 may begin at step 1902. At step 1902, the user may remove the fitting and the capped pre-filled syringe from the sterile packaging.

At step 1904, the user may invert the capped syringe so that the capped end is approximately upright.

At step 1906, the user may uncap the inverted syringe.

At step 1908, the user may fully engage the uncapped inverted syringe into the fitting. In embodiments in which the syringe includes the seal, the fitting may support a needle and include a reservoir but may be configured such that it does not include a seal. In embodiments in which the syringe includes the reservoir, the fitting may support a needle but may be configured such that it does not include a reservoir. Engagement of the syringe with the fitting may effect sealing contact of the syringe and the fitting.

At step 1910, the user may remove the needle guard from the fitting.

At step 1912, the user may depress the plunger of the inverted syringe. Depression of the plunger may advance the distal face of the plug within the syringe bore from $L_{prefill}$ to $L_{primed}$ (shown in FIG. 17). Advancement of the distal face of the plug may reduce the volume of fluid within the syringe by $V_{primed}$. Advancement of the distal face of the plug may prime the syringe engaged with the fitting.

Advancement of the plunger within the bore may be limited by the shaft collar (shown in FIG. 16). After advancement of the shaft to $L_{primed}$ (shown in FIG. 17), the user may remove the collar.

At step 1914, the user may insert the needle into a target area, such as target 1880 (shown in FIG. 18).

At step 1916, the user may fully depress the plunger to the maximum delivery stroke, injecting the dose volume of medicament into the target area.

Thus, apparatus and methods for low-volume medicament delivery have been provided. Persons skilled in the art will appreciate that the present invention can be practiced by other than the described embodiments, which are presented for purposes of illustration rather than of limitation. The present invention is limited only by the claims that follow.

What is claimed is:

1. A fitting for a fluid dispenser, the fitting having a longitudinal axis and comprising:
   a detent that is configured to limit longitudinal insertion of the dispenser into the fitting by contacting a terminal surface of the dispenser, a top of the detent defining a first tangent plane;
   a seal that is configured to be deformed by the surface, into a sealing contact against the surface, the contact defining a second tangent plane substantially coplanar with the first plane when the surface abuts the detent, the first plane maintaining a fixed orientation relative to the top throughout deformation of the seal; and
   a body that is configured to:
   receive the surface; and
   support the detent and the seal;

wherein;
  the seal is seated in the body in a recess having a bottom; and
  the body includes an interior proximal-facing facet that is disposed;
    more proximal than is the bottom; and
    more distal than is the top.

2. The fitting of claim 1 wherein the detent defines an opening configured to be placed in fluid communication with the dispenser.

3. The fitting of claim 2 wherein the opening is configured to be placed in fluid communication with an aperture of the dispenser when the surface lodges against the decent.

4. The fitting of claim 1 wherein the seal circumscribes detent.

5. The fitting of claim 1 wherein the detent circumscribes the seal.

6. The fitting of claim 2 wherein:
  the body includes an interior wall; and
  the dispenser includes a lateral wall;
such that, when the surface is in sealing contact against the seal, and abuts the detent, the interior wall, the lateral wall and the seal define a region that is isolated from fluid communication with the dispenser.

7. The fitting of claim 6 wherein:
  the region is a first dead space having a first volume;
  the detent, when in contact with the surface, defines a second dead space having a second volume; and
  the second volume is no more than 1% the first volume.

8. The fitting of claim 7 wherein the second dead space includes one or more volumes in a region that is:
  transversely coextensive with contact between the surface and the detent; and
  longitudinally extensive between the surface and the detent.

9. The fitting of claim 7 wherein the second dead space is within the seal.

10. The fitting of claim 6 wherein the sealing contact is sufficient to prevent leakage of fluid from the dispenser to the region when the dispenser is actuated to dispense the fluid.

11. The fitting of claim 6 wherein the interior wall includes a boss that is configured to engage the lateral wall of the dispenser.

12. The fitting of claim 2 wherein:
  the dispenser is pre-filled with an initial volume of fluid; and
  the body defines a void that is in fluid communication with the opening, the void having a void volume that is not less than 10% the initial volume.

13. The fitting of claim 12 wherein the void volume is not less than 25% the initial volume.

14. The fitting of claim 12 wherein the void volume is not less than 50% the initial volume.

15. The fitting of claim 12 wherein the void volume is not less than 75% the initial volume.

16. The fitting of claim 12 wherein the void volume is not less than 90% the initial volume.

17. The fitting of claim 12 wherein a volume of fluid dispensed through an orifice of a needle in fluid communication with the void is the initial volume reduced by an amount that is not less than the void volume.

18. The fitting of claim 1 wherein the seal is annular.

19. The fitting of claim 1 wherein:
  the seal includes a proximal face; and
  the seal includes a distal face, spaced apart from the proximal face.

20. The fitting of claim 19 wherein the proximal face and the distal face are substantially parallel.

21. The fitting of claim 19 wherein:
  the seal includes an outer surface that extends in the longitudinal direction; and
  the seal includes an inner surface that extends in the longitudinal direction.

22. The fitting of claim 21 wherein:
  the distal face and the inner surface intersect at an angle of about 90°; and
  the distal face and the outer surface intersect at an angle of about 90°.

23. The fitting of claim 1 further including a base portion from which the detent and the seal extend longitudinally in a proximal direction, the detent including the top, the seal, in a relaxed state, extending proximally beyond the top.

24. The fitting of claim 23 wherein the seal does not extend transversely over the top.

25. The fitting of claim 1 wherein the recess is configured to secure the seal such that a proximal end of the seal is not drawn laterally over the top.

26. The fitting of claim 1 wherein the axis, when the surface abuts the detent, lies perpendicular to the surface.

27. The fitting of claim 1 wherein:
  the detent has a first contour;
  the surface has a second contour; and
  the first contour and the second contour are complementary.

28. The fitting of claim 27 wherein;
  the seal has a third contour; and
  the second contour and the third contour are complementary.

29. The fitting of claim 1 wherein:
  the seal comprises a first substance that has a first elastic modulus;
  the detent comprises a second substance that has a second elastic modulus; and
  the second elastic modulus is greater than the first elastic modulus.

30. The fitting of claim 29 wherein the surface is disposed on a portion of the dispenser having a third elastic modulus.

31. The fitting of claim 30 wherein the third elastic modulus is about the same as the second elastic modulus.

32. The fitting of claim 1 further comprising an engagement member that is configured to maintain the sealing contact by engaging the dispenser.

33. The fitting of claim 1 wherein the fitting is configured to engage a needle guard.

* * * * *